(12) United States Patent
Tsai et al.

(10) Patent No.: US 10,265,502 B2
(45) Date of Patent: Apr. 23, 2019

(54) ADJUSTABLE STIFFNESS CATHETER

(71) Applicant: Beth Israel Deaconess Medical Center, Inc., Boston, MA (US)

(72) Inventors: Leo Lee Tsai, Arlington, MA (US);
Yuyin Chen, Cambridge, MA (US);
Vyas Ramanan, Cambridge, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 0 days.

(21) Appl. No.: 14/828,965

(22) Filed: Aug. 18, 2015

(65) Prior Publication Data
US 2016/0136393 A1 May 19, 2016

Related U.S. Application Data

(63) Continuation-in-part of application No. 14/184,427, filed on Feb. 19, 2014, which is a continuation of
(Continued)

(51) Int. Cl.
*A61M 25/00* (2006.01)
*A61B 1/00* (2006.01)
(Continued)

(52) U.S. Cl.
CPC ......... *A61M 25/0054* (2013.01); *A61B 1/005* (2013.01); *A61B 1/0055* (2013.01);
(Continued)

(58) Field of Classification Search
CPC .......... A61M 25/0054; A61M 25/0141; A61M 2025/0062; A61M 2025/0063; A61M 2025/0175; A61F 2/95
See application file for complete search history.

(56) References Cited

U.S. PATENT DOCUMENTS

| 4,662,404 A | 5/1987 | LeVeen et al. |
| 4,945,920 A * | 8/1990 | Clossick ............... A61B 10/06 600/564 |

(Continued)

FOREIGN PATENT DOCUMENTS

| WO | 2007/028058 A2 | 3/2007 |
| WO | 2007/057132 A1 | 5/2007 |

(Continued)

OTHER PUBLICATIONS

Kiyosue, H et al., "Shapability, Memory, and Luminal Changes in Microcatheters after Steam Shaping: A Comparison of 11 Different Micorcatherters." Am. J. Neuroradiol, 2005, 26: 2610-2616.
(Continued)

*Primary Examiner* — Andrew M Gilbert
(74) *Attorney, Agent, or Firm* — McCarter & English, LLP; Thomas O. Hoover

(57) ABSTRACT

The present invention relates to a catheter that has adjustable stiffness that enables a user to select the stiffness of at least one region of the catheter during insertion and navigation through a body lumen. A preferred embodiment of the invention works in combination with a guidewire to enable placement of the catheter at a position within the vascular system, for example, to enable treatment of a variety of medical conditions. The catheter can include segments that undergo relative movement in response to actuation by the user to adjust the flexibility of the at least one region, preferably located at or near the distal end of the catheter.

15 Claims, 28 Drawing Sheets

Related U.S. Application Data application No. PCT/US2014/017179, filed on Feb. 19, 2014.

(60) Provisional application No. 62/038,628, filed on Aug. 18, 2014, provisional application No. 61/766,527, filed on Feb. 19, 2013.

(51) Int. Cl.

| | |
|---|---|
| *A61B 1/005* | (2006.01) |
| *A61M 25/01* | (2006.01) |
| *A61M 25/09* | (2006.01) |
| *A61F 2/95* | (2013.01) |
| *A61B 17/12* | (2006.01) |
| *A61B 17/00* | (2006.01) |
| *A61F 2/958* | (2013.01) |

(52) U.S. Cl.
CPC ..... *A61B 1/00071* (2013.01); *A61M 25/0009* (2013.01); *A61M 25/0013* (2013.01); *A61M 25/0043* (2013.01); *A61M 25/0108* (2013.01); *A61M 25/0136* (2013.01); *A61M 25/0138* (2013.01); *A61M 25/0147* (2013.01); *A61M 25/09* (2013.01); *A61B 17/1214* (2013.01); *A61B 17/12186* (2013.01); *A61B 2017/00305* (2013.01); *A61B 2017/1205* (2013.01); *A61F 2/95* (2013.01); *A61F 2/958* (2013.01); *A61M 2025/0004* (2013.01); *A61M 2025/0062* (2013.01); *A61M 2025/0063* (2013.01); *Y10T 156/1062* (2015.01)

(56) References Cited

U.S. PATENT DOCUMENTS

| | | | |
|---|---|---|---|
| 5,222,949 A * | 6/1993 | Kaldany | A61L 29/042 600/433 |
| 5,290,229 A | 3/1994 | Paskar | |
| 5,334,171 A * | 8/1994 | Kaldany | A61L 29/042 604/20 |
| 5,337,733 A * | 8/1994 | Bauerfeind | A61B 1/00071 600/114 |
| 5,531,685 A | 7/1996 | Hemmer et al. | |
| 5,538,512 A | 7/1996 | Zenzon et al. | |
| 5,632,734 A * | 5/1997 | Galel | A61M 25/0041 138/120 |
| 5,662,621 A * | 9/1997 | Lafontaine | A61M 25/0041 604/164.13 |
| 5,779,669 A | 7/1998 | Haissaguerre et al. | |
| 6,036,682 A | 3/2000 | Lange et al. | |
| 6,097,976 A | 8/2000 | Yang et al. | |
| 6,790,173 B2 * | 9/2004 | Saadat | A61B 1/0008 600/114 |
| 7,507,229 B2 | 3/2009 | Hewitt et al. | |
| 7,618,411 B2 | 11/2009 | Appling | |
| 7,717,899 B2 | 5/2010 | Bowe et al. | |
| 7,766,896 B2 | 8/2010 | Kornkven Volk et al. | |
| 7,815,975 B2 | 10/2010 | Pursley | |
| 7,828,790 B2 | 11/2010 | Griffin | |
| 7,935,108 B2 | 5/2011 | Baxter et al. | |
| 7,998,132 B2 | 8/2011 | Gregorich et al. | |
| 8,012,117 B2 | 9/2011 | Bonnette et al. | |
| 8,083,713 B2 | 12/2011 | Smith et al. | |
| 8,231,551 B2 | 7/2012 | Griffin et al. | |
| 8,303,570 B2 | 11/2012 | Gregorich et al. | |
| 8,328,791 B2 | 12/2012 | Griffin | |
| 8,641,748 B2 | 2/2014 | Hebert et al. | |
| 8,876,772 B2 | 11/2014 | Weber et al. | |
| 2001/0001812 A1 | 5/2001 | Valley et al. | |
| 2001/0016725 A1 | 8/2001 | Valley et al. | |
| 2003/0236445 A1 * | 12/2003 | Couvillon, Jr. | A61M 25/0105 600/114 |
| 2004/0006302 A1 * | 1/2004 | Chaouk | A61M 25/0009 604/40 |
| 2004/0054322 A1 | 3/2004 | Vargas | |
| 2005/0004556 A1 | 1/2005 | Pursley | |
| 2005/0027249 A1 | 2/2005 | Reifart et al. | |
| 2005/0148997 A1 | 7/2005 | Valley et al. | |
| 2006/0079923 A1 | 4/2006 | Chhabra et al. | |
| 2006/0106447 A1 * | 5/2006 | Opolski | A61B 17/0057 623/1.11 |
| 2006/0129130 A1 | 6/2006 | Tal et al. | |
| 2006/0129178 A1 | 6/2006 | Reifart et al. | |
| 2006/0184105 A1 | 8/2006 | Townsend et al. | |
| 2007/0112331 A1 * | 5/2007 | Weber | A61L 29/041 604/530 |
| 2007/0250149 A1 * | 10/2007 | Von Oepen | A61F 2/958 623/1.11 |
| 2007/0270779 A1 | 11/2007 | Jacobs et al. | |
| 2008/0009831 A1 * | 1/2008 | Griffin | A61M 25/005 604/531 |
| 2008/0065013 A1 | 3/2008 | Goodin | |
| 2008/0097399 A1 | 4/2008 | Sachar et al. | |
| 2008/0172037 A1 * | 7/2008 | Huang | A61M 25/0043 604/526 |
| 2009/0018502 A1 | 1/2009 | Reifart et al. | |
| 2010/0241185 A1 | 9/2010 | Mahapatra et al. | |
| 2011/0106055 A1 | 5/2011 | Robertson | |
| 2011/0238041 A1 | 9/2011 | Lim et al. | |
| 2011/0313402 A1 * | 12/2011 | Morero | A61M 25/0041 604/528 |
| 2012/0253193 A1 | 10/2012 | Hanson et al. | |
| 2013/0012923 A1 | 1/2013 | Baxter et al. | |
| 2013/0012924 A1 | 1/2013 | Davis et al. | |
| 2013/0085479 A1 | 4/2013 | de la Rama et al. | |
| 2014/0236120 A1 | 8/2014 | Tsai et al. | |
| 2015/0196732 A1 | 7/2015 | Gregorich et al. | |

FOREIGN PATENT DOCUMENTS

| | | |
|---|---|---|
| WO | 2008/057839 A2 | 5/2008 |
| WO | 2010/014882 A1 | 2/2010 |
| WO | 2012/094135 A2 | 7/2012 |

OTHER PUBLICATIONS

International Search Report on Application PCT/US2014/017179, dated Apr. 1, 2014.

* cited by examiner

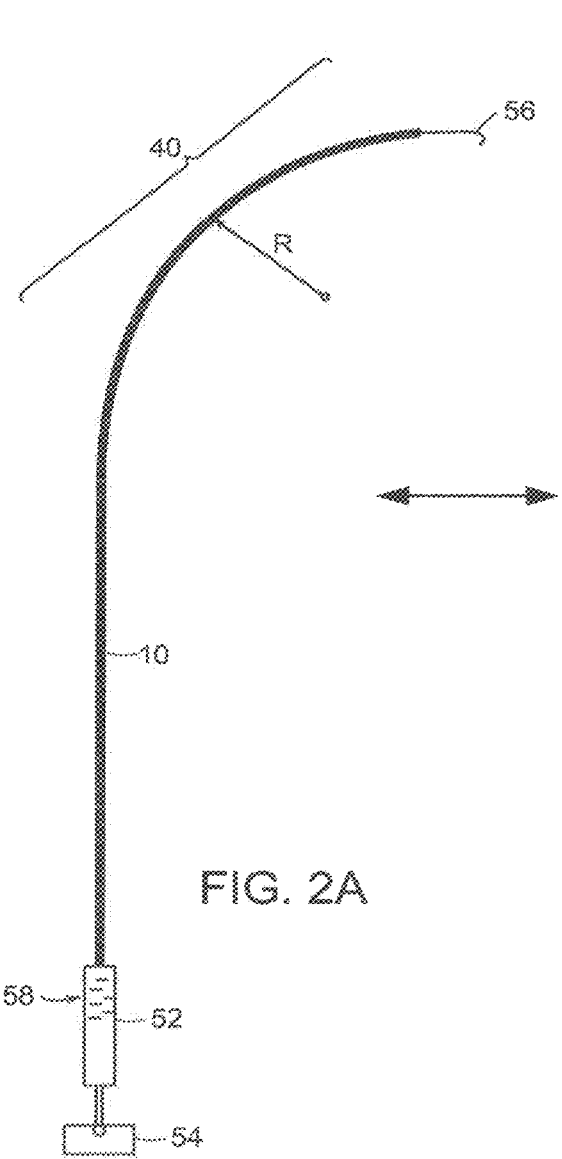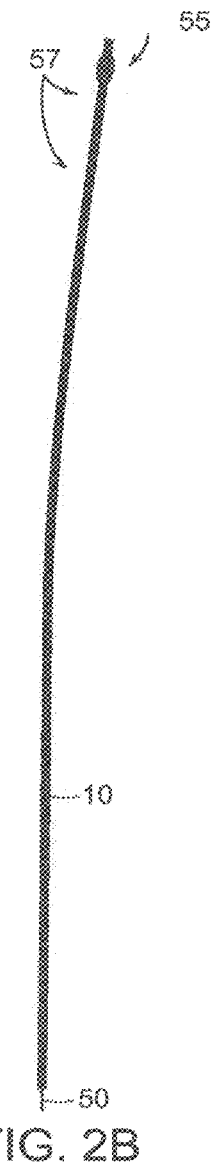
FIG. 2A
FIG. 2B

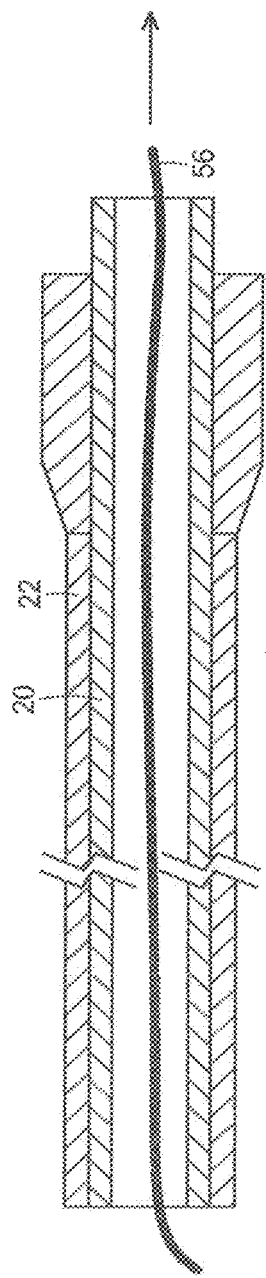
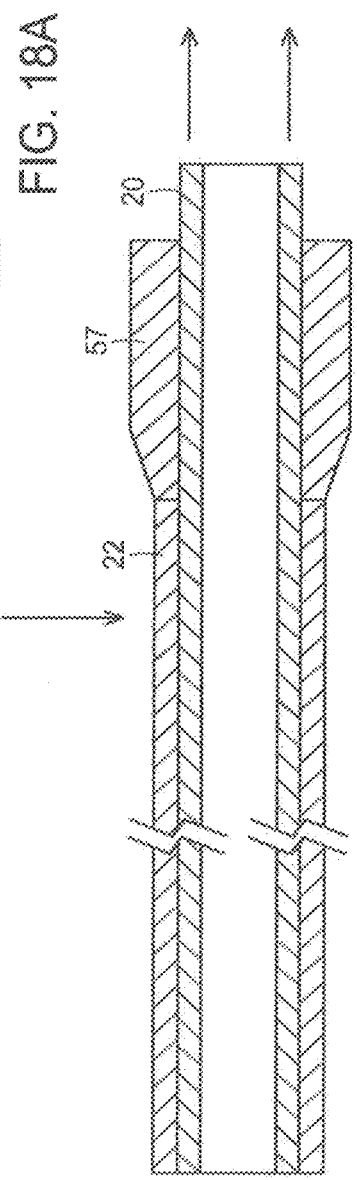
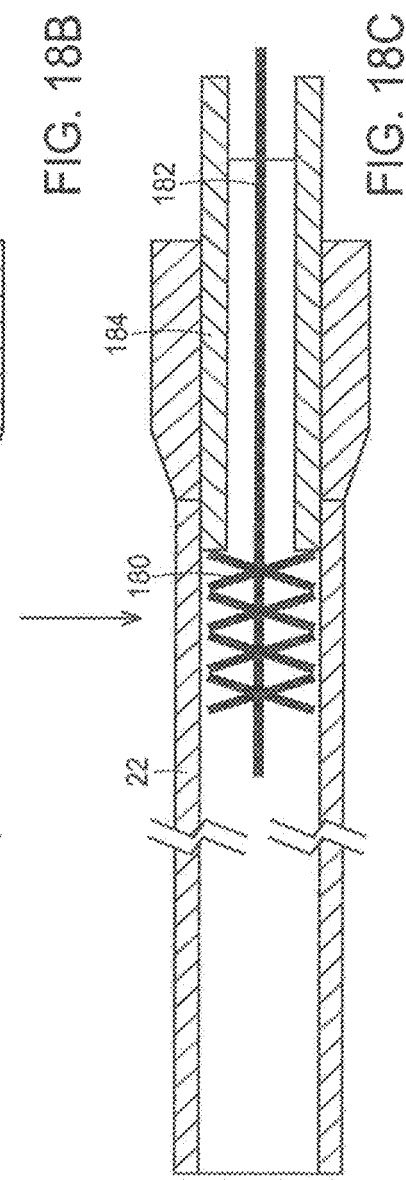

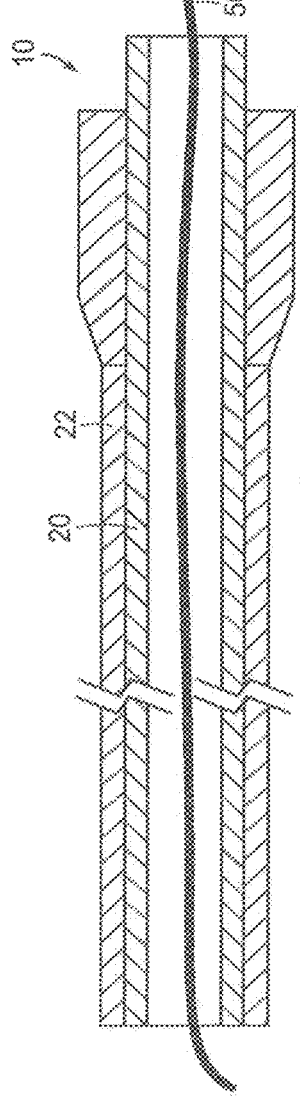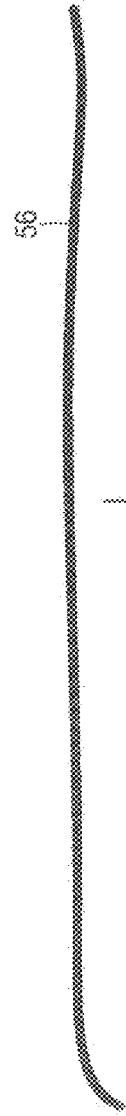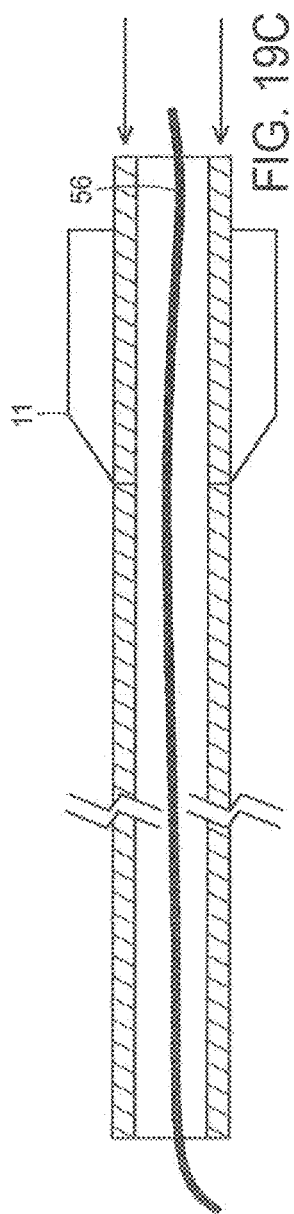

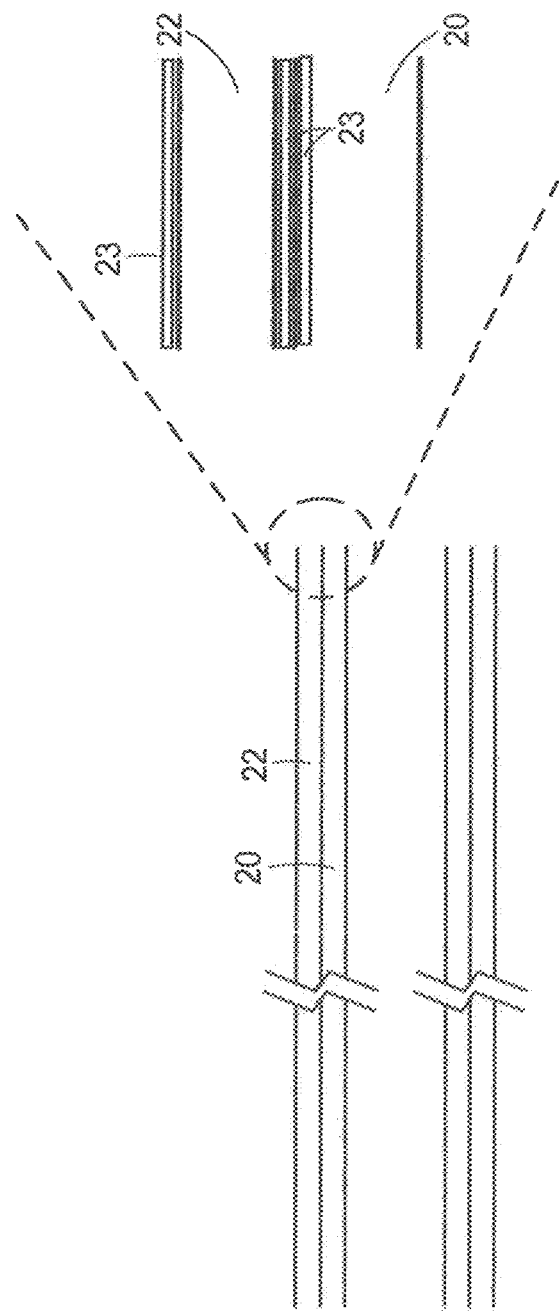

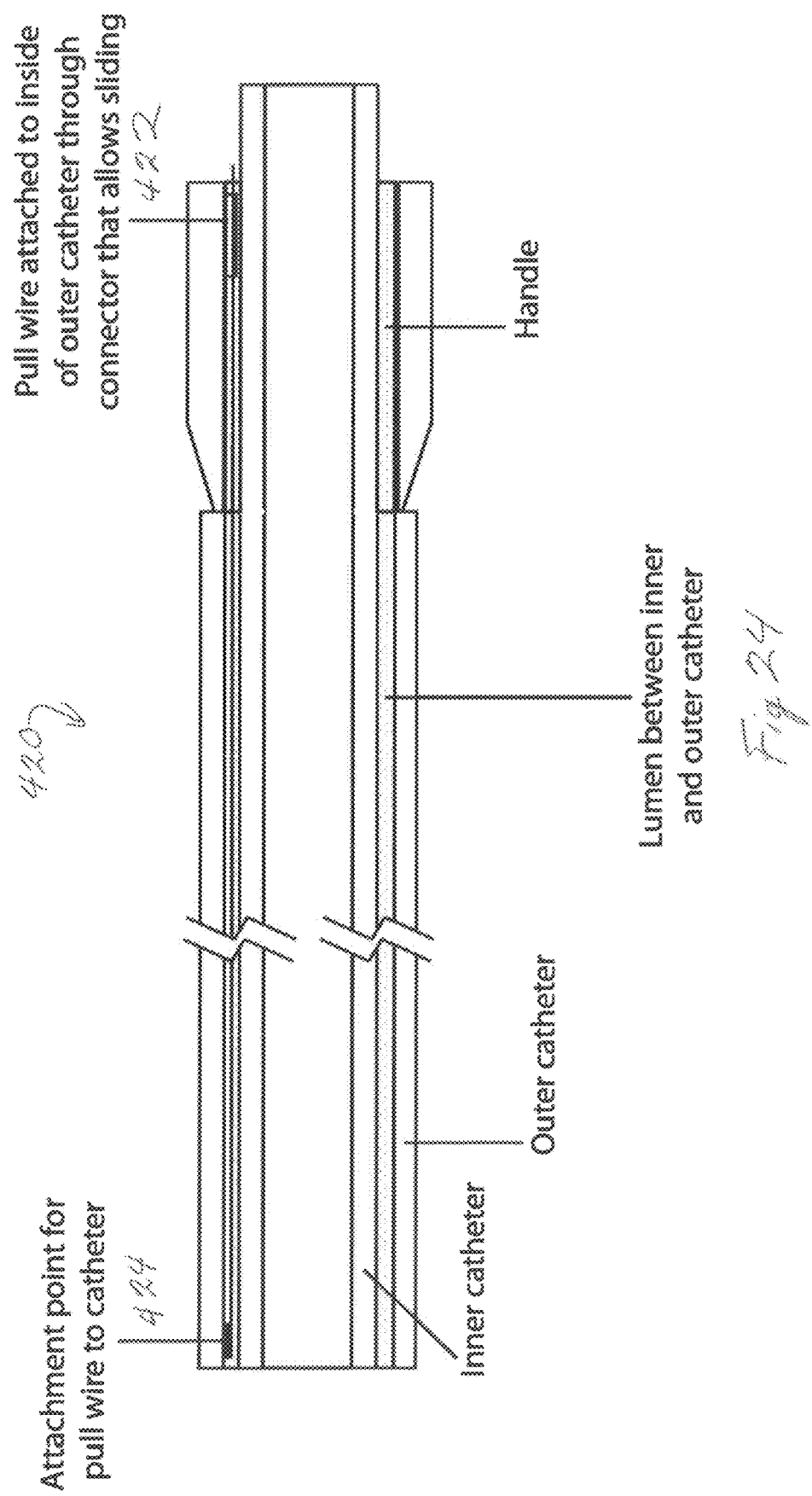

ADJUSTABLE STIFFNESS CATHETER

CROSS REFERENCE TO RELATED APPLICATION

This application is a continuation-in-part of U.S. application Ser. No. 14/184,427 filed Feb. 19, 2014, and claims priority to International Application PCT/US2014/017179 filed Feb. 19, 2014 and to U.S. Provisional Application No. 61/766,527 filed Feb. 19, 2013 and also claims priority to U.S. Provisional Application No. 62/038,628 filed Aug. 18, 2014, the entire contents of the above applications being incorporated herein by reference.

BACKGROUND OF THE INVENTION

The present invention relates to variable stiffness catheters and more specifically relates to devices and methods for accessing tubular structures in the body. Existing catheters commonly use a guidewire to aid in the positioning thereof within body lumens for the purpose of delivering medical devices or therapeutic agents to treat a variety of medical conditions. Often, the delivery path within the lumens or vessels of a mammalian body can include regions under 2 mm in diameter and may require the distal end of the device to undergo turns of 90 degrees or more to reach the region requiring treatment. Many vascular applications involving the treatment of strokes, aneurysms, or embolizations, for example, involve navigation through the turns that are required, while catheters that are too flexible may kink and thereby complicate proper placement within the body. There are also risks of vessel perforation or vasospasm in procedures that are frequently time sensitive.

Many available catheters have fixed variable stiffness in which the proximal end is stiffer than the distal end. This improves the pushability of the device and also allows the distal end to bend at the required angles. Some devices are made with materials that are preshaped, or alternatively, permit steam shaping of the distal end to improve navigational performance. However, existing devices continue to be limited in the capabilities needed to access small remote locations requiring treatment. Thus, a continuing need exists for improvements in catheter design that enable fast and safe delivery of various treatment options within the mammalian body.

SUMMARY OF THE INVENTION

The invention generally relates to a catheter having adjustable stiffness in which the user can select a level of stiffness to enable navigation within lumens of a mammalian body. A preferred embodiment can include a tubular body with at least two portions or layers that are able to move relative to each other. Relative motion of the two portions of the tubular body changes the stiffness of at least one region of the catheter such that the at least one region can bend at an angle relative to the longitudinal axis of the catheter. In a preferred embodiment, each of the plurality of layers can include segments of different lengths, materials, and/or durometer rating.

The catheter can include an inner tube and an outer tube that slide relative to each other by manual actuation. The inner tube has a distal portion with a first plurality of spaced regions having a first stiffness. The spaced regions can be separated by a corresponding plurality of spaced segments having a greater stiffness than the spaced regions. These alternating stiff and flexible elements of the inner tube can be moved longitudinally relative to an outer tube that has alternating segments and regions of differing stiffness. This operates to alter the overall state of flexibility of a distal portion of the catheter. An important metric that reflects this flexibility is the minimum radius of curvature of the flexible portion of the catheter that is associated with a selected relative position of the adjustable catheter elements. For preferred embodiments, the minimum radius of curvature is in a range of 2-6 mm and preferably in a range of 3-5 mm.

A preferred embodiment includes an actuator or switch to change the position of the layers of the tube relative to each other. The actuator can be mounted on a handle positioned at a proximal end of the catheter, which can also include other operative elements to perform selected modes of treatment within the vascular system, for example. The catheter can include a central lumen having a diameter such that a guidewire can slide into the proximal or distal opening of the catheter lumen.

Thus, preferred embodiments of the present invention provide access to tubular structures in the body with high tortuosity and can be used for accessing vessels that perfuse the central nervous system, the abdomen, the pelvis, the cardiovascular system, the respiratory system, peripheral vessels, the gastrointestinal system, the genitourinary tract and the neurovascular system. The catheter can be inserted into body lumens, or alternatively, by percutaneous entry with an introducer.

Preferred embodiments of the invention can include a plurality of treatment devices and methods that can be delivered to anatomic sites within the human or animal body. Devices for treatment of the vascular system can include stents, filters and/or balloon devices, for example. Medications can be delivered with the catheter through one or more channels within the catheter or in combination with the above referenced devices. The handle can include one or more side ports to introduce devices and or medications.

Preferred embodiments of the invention also relate to methods of manufacturing adjustable stiffness catheters. The inner and outer tubes can be made with a coiled or braided structure. A preferred embodiment can include steps of forming annular segments of differing stiffness, arranging the segments in a selected order, and heating the segments to thereby form the inner and outer tubes such that the segments are arranged to provide the desired range of flexibility.

Other objects and advantages of the present invention will become apparent to the reader, and it is intended that these objects and advantages are within the scope of the present invention. To the accomplishment of the above and related objects, this invention may be embodied in the form illustrated in the accompanying drawings, attention being called to the fact, however, that the drawings are illustrative only, and that changes may be made in the specific construction illustrated and described within the scope of this application.

BRIEF DESCRIPTION OF THE DRAWINGS

FIGS. 2A-2B are side views of flexible and rigid states of a catheter body in accordance with the present invention;

FIGS. 18A-18C illustrate side cutaway views of a catheter used to deliver a stent to a treatment site according to certain embodiments of the present disclosure;

FIGS. 19A-19C illustrate a method of positioning a second catheter or treatment device using various embodiments of the present invention;

FIGS. 22A-22B illustrate side cutaway views of catheters incorporating lubricious coatings, according to various embodiments;

FIG. 24 is a cross-sectional view of a further embodiment of catheter with a pull wire for directional control in accordance with preferred embodiments;

DETAILED DESCRIPTION OF THE INVENTION

Figure 1D:
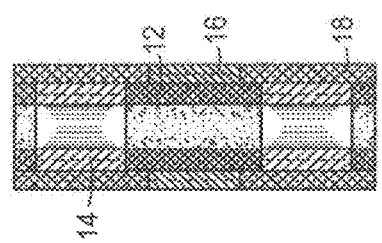
FIGS. 1A-1D are side views of flexible and rigid states, respectively, of preferred embodiments of the present invention.
Figure 1C:
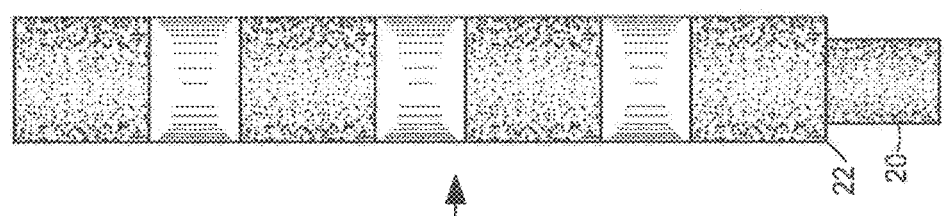
Figure 1B:
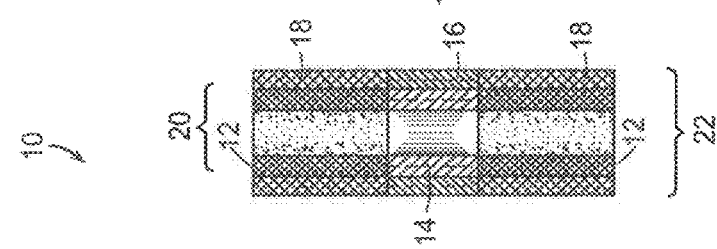
Figure 1A:
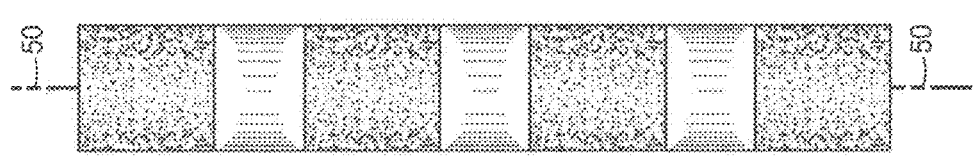

Turning now to a description of the drawings, in which similar reference characters denote similar elements throughout the several views, FIGS. 1A-1D illustrate a tube 10 with at least two layers 20,22 that are able to slide past each other, each of which includes a plurality of segments 12,14 and 16,18 that can have different lengths, materials, and/or durometer rating. The device 10 can further comprise an actuator such as a mechanical switch, to change the relative positioning of the layers of the tube relative to each other.

The outer tube layer 22 can have segments 16,18 of different lengths, materials, and/or durometer ratings. In the preferred embodiment, the outer layer 22 comprises two alternating segments 16,18, each with its own characteristic length, material(s), and durometer ratings. In some embodiments, the length of the segment with higher durometer rating 18 will be greater than that of the segment with the lower durometer rating 16.

Segment materials can comprise (but are not limited to) FEP, PFA, Pebax, polyurethane, nylon, PVC, TPE, polyester. The catheter elements may be formed by methods including, but not limited to, extrusion or casting. Segment or layer reinforcing material may include a metal such as, but not limited to, 304 SS, 316 SS, and/or monofilament materials.

The segments may be of appropriate length, be made of appropriate material(s), and have any appropriate durometer rating required for a given application. Catheters having lengths ranging from 10 cm to 2 m, and diameters of less than 1 mm to more than 10 mm, can be made in accordance with preferred embodiments of the invention. Small diameter guide catheters can be less than 2 mm in diameter in the distal region and preferably less than 1 mm.

The outer layer 22 can comprise two types of segments (each with a characteristic length, material composition, durometer rating) that alternate. It can also comprise selected combinations of different segments. The length of the segment with higher durometer rating (18) can be greater than, equal to, or less than that of the segment with the lower durometer rating (16).

The inner tube layer 20 has segments of different lengths, materials, and/or durometer ratings. In the preferred embodiment, the outer layer comprises two alternating segments 12 and 14, each with its own characteristic length, material(s), and/or durometer ratings. The length of the segment with higher durometer rating (12) can be greater than that of the segment with the lower durometer rating (14). The length of segment 12 can equal that of 18 and the length of segment 14 can equal that of 16, for example.

Segment materials can comprise, but are not limited to, FEP, PFA, pebax, polyurethane, nylon, PVC, TPE, polyester. The catheter may be formed by methods including, but not limited to, extrusion or casting. Segment reinforcing material may include a metal, nitinol, or specifically stainless steel, such as, but not limited to: 304 SS, 316 SS, or can comprise one or more monofilaments. Thus, one or more components of the catheter can comprise a shape memory material. The catheter can include a curved distal tip to assist with steering of the device.

The inner layer 20 can comprise two types of segments (each with a characteristic length, material composition, durometer rating) that alternate. It may also comprise a combination of any number of different segments. The length of the segment with higher durometer rating (12) can be greater than, equal to, or less than that of the segment with the lower durometer rating (14).

The inner layer 20 can also take the form of a wire instead of a tube where the application does not require a central lumen for a guidewire or to provide a port for insertion of fluids such as a flushing liquid, or for delivery of medication, or to introduce other tools or devices through, or with, the catheter.

An actuator used for adjusting catheter stiffening can comprise a sliding device that allows the inner and outer layers of the tube to be switched from a position in which segments 12 and 18 are in register and 14 and 16 are in register, to a position in which they are out of register where the segment 12 bridges the gap between adjacent segments 18 (FIG. 1D). In the in-register state (FIG. 1B), the flexibility of the overall tube is dictated by the less stiff segments 14 and 16. In the out of-register state, the flexibility of the overall tube is dictated by the more stiff segments 12 and 18.

As shown in FIGS. 2A and 2B, the catheter body 10 can have a flexible region 40 in which segments are registered such that the flexible region 40 can bend along a selected radius of curvature R. The catheter 10 can include a handle 52 mounted at a proximal end that can have a plurality of actuators, buttons, or switches 58 that are operative to change the flexibility of all or a portion of the catheter. A slider element can also be used to advance a guidewire 56 that can be inserted into a central lumen of the catheter. The guidewire 56 can have a distal hook, or "J" shaped distal end, that can allow the user to select one of a plurality of branches of an arterial system. The guidewire can be used with the adjustable catheter to navigate the many branches of the neurovascular system, for example, to deliver treatment or aid in the imaging of a particular treatment site. A fluid source 54 can be used to deliver a fluid such as a contrast agent, a medication, nutrients, electrolytes, blood products, chemotherapy agents or radiotherapy agents, for example. As shown in FIG. 2B, the catheter in its more rigid state has limited flexibility and is generally aligned along its longitudinal axis 50. The catheter 10 can include a device 55, such as a stent or balloon, which can be positioned with the catheter at a treatment site. Fluoroscopic markers 57 can be included to aid in visualization.

Figure 2C:
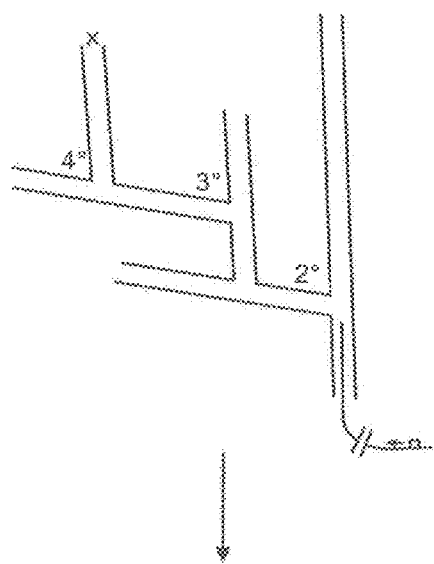
FIGS. 2C-2F illustrate a process of advancing the catheter through a series of branching features of a lumen system to a treatment site.
Figure 2F:
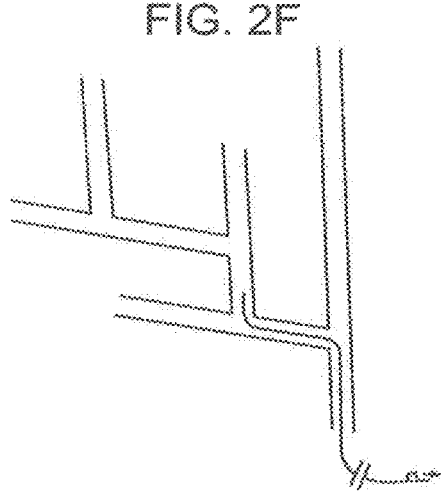
Figure 2D:
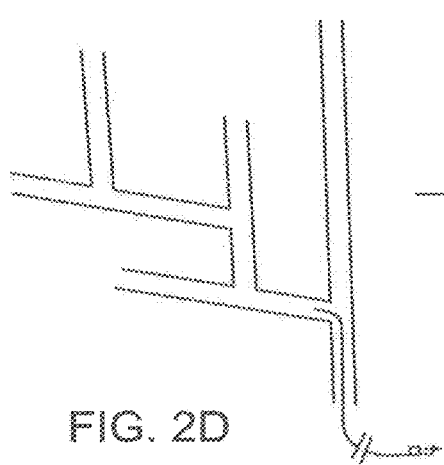
Figure 2E:
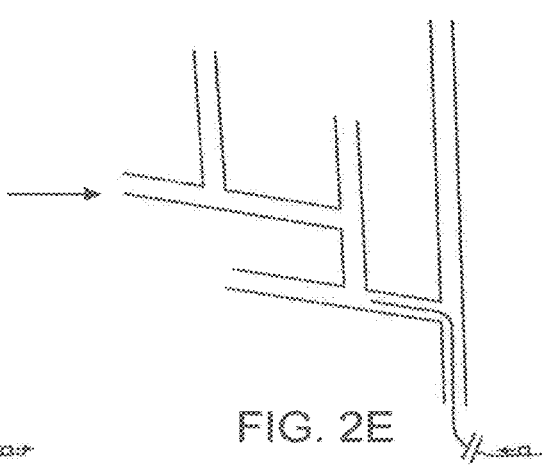

However, as illustrated in the sequence of FIGS. 2C-2F, the catheter is used to bend in different directions where the more flexible state is used to initiate turns and a more rigid state to advance along more linear regions of a lumen system. Note that the catheter can simply switch back and forth between two states (rigid and flexible) or alternatively, the user can select a level of stiffness from a continuum of available levels depending on the sizes and locations of the second, third, or fourth degree turns that can be encountered, as illustrated in FIG. 2C. The catheter can be initially stiff upon percutaneous introductions, is adjusted to a flexible state at the first turn (FIG. 2D) is made rigid while advancing to the next turn (FIG. 2E) and made flexible to initiate the second turn at FIG. 2F. This process is continued through the third and fourth turns, as needed, to reach the treatment site.

Figure 3A:
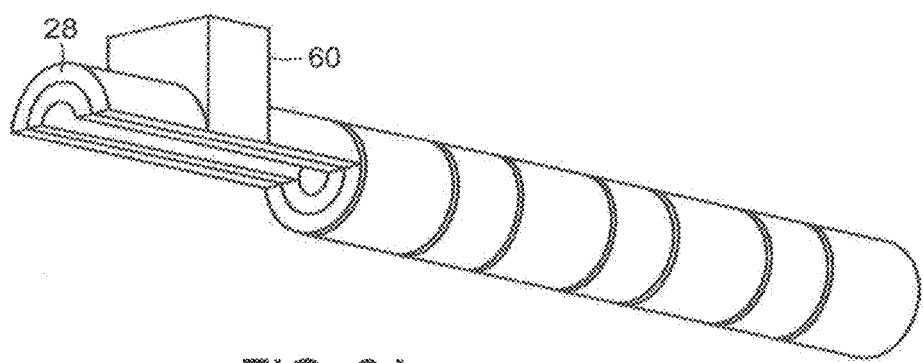
FIGS. 3A-3B are partial cutaway perspective views of an actuator such as a sliding switch to adjust between flexible and stiff states in accordance with the present invention.
Figure 3B:
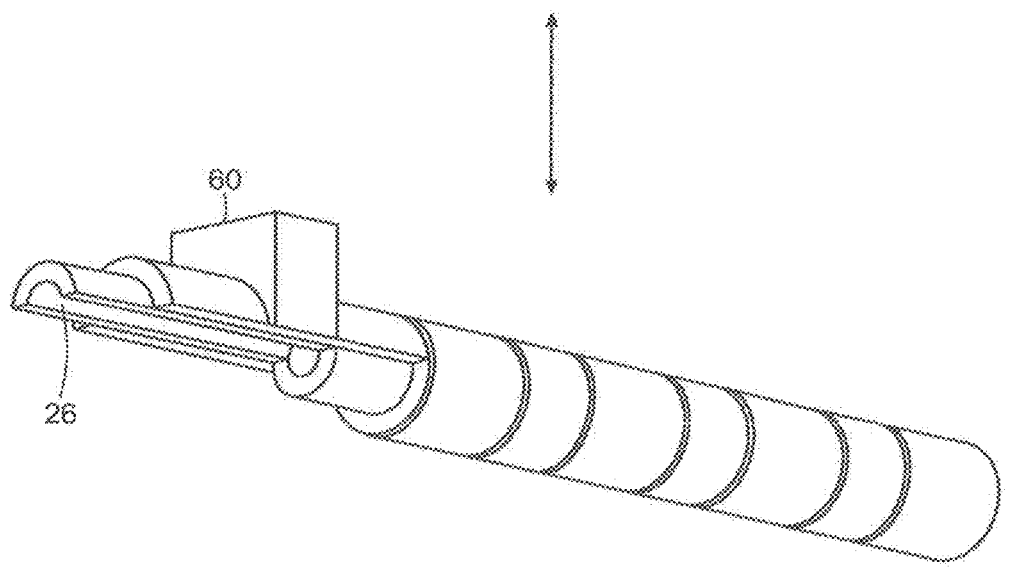
Figures 4A, 4B:
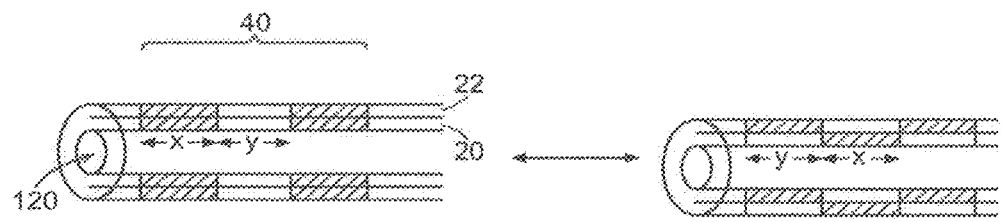
FIGS. 4A-4I illustrate embodiments of a sliding two-layer system for an adjustable stiffness catheter in accordance with preferred embodiments of the invention.
Figure 4C:
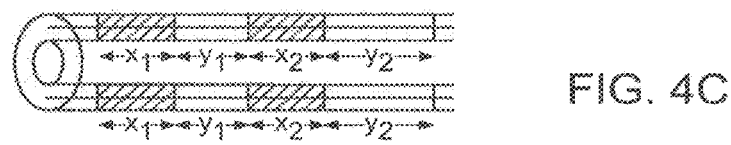
Figure 4D:
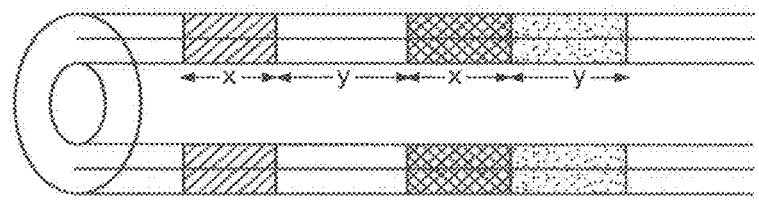
Figure 4E:
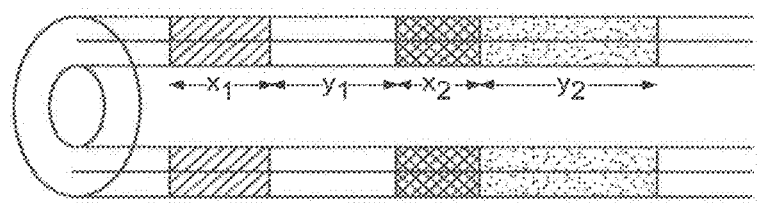
Figure 4F:
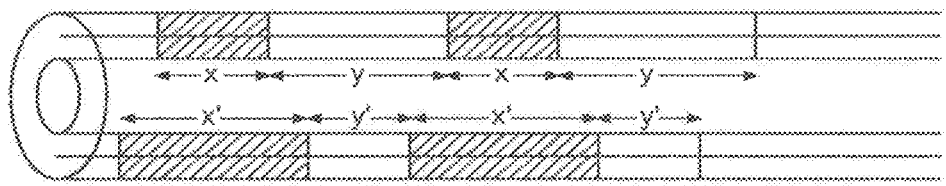
Figure 4G:
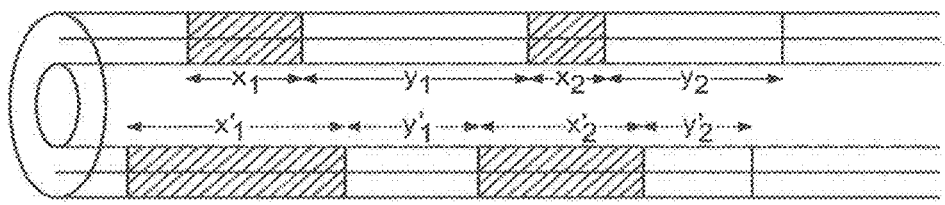
Figure 4H:
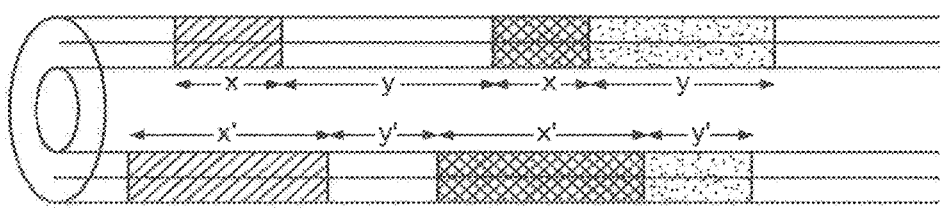
Figure 4I:
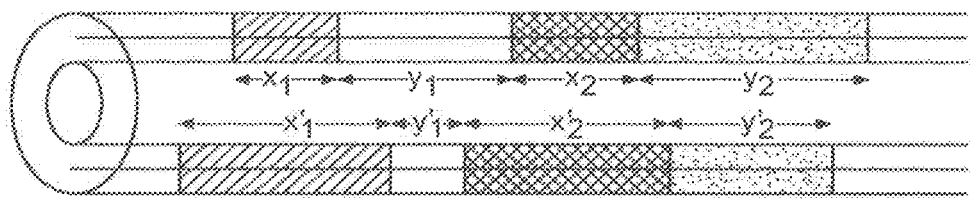
Figure 4J:
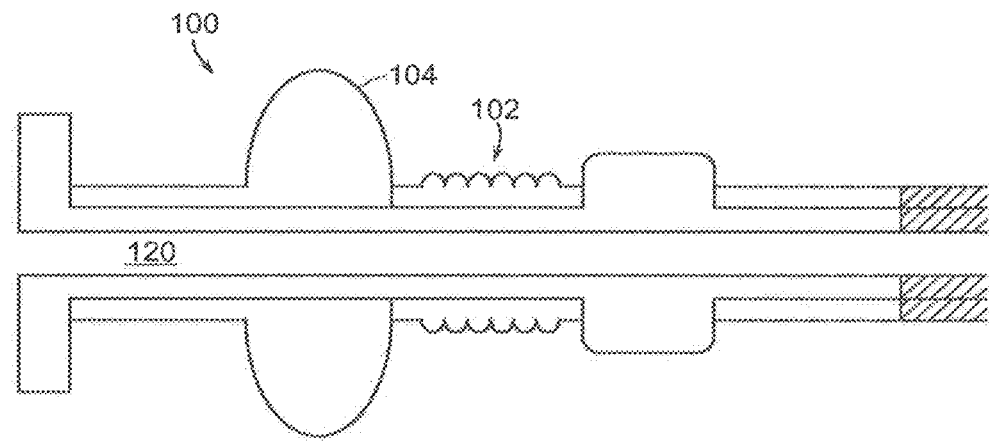
FIGS. 4J-4K illustrate a spring-operated actuator in accordance with certain embodiments of the invention.
Figure 4K:
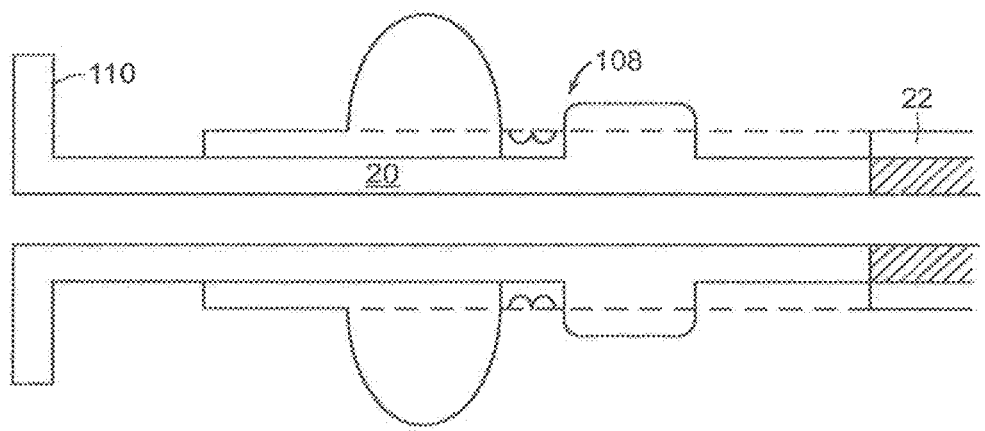

As shown in FIGS. 3A-3B, an actuator such as a slider switch device 60 can comprise a base 26 that can slide relative to the outer layer 28 wherein the user can manually engage the slider element 60 that is connected to the outer layer 28 (see FIGS. 4J-4K, hereinafter, for example).

The inner and outer layers 20,22 of the tube 10 are concentric and can slide past each other in this embodiment. The switch 60 is connected to the two layers 20,22 of the tube, with the base connected to the inner layer 20 of the tube, and a slider 60 connected to the outer layer of the tube. This switch 60 allows the outer layer to slide longitudinally over the inner layer.

The tube 10 is comprised of inner and outer layers 20,22, each consisting of alternating flexible segments of length x and semi-rigid segments of length y. The inner and outer layers 20,22 of the tube 10 can comprise either two concentric tubes with differing radii, or a combination of a tube and wire. The alternating segments can be made of materials, have a selected thickness, have a selected tensile strength, and have a selected shear modulus to achieve the desired thickness and radius of curvature required for a given application. The inner and outer layers 20,22 will move longitudinally against each other in a controlled manner, via a mechanical switching device. When the alternating stiff and flexible segments of the inner and outer layers of the catheter tube are in register, the catheter tube is in a "relaxed" flexible state. When the segments are out of register, the rigid segments of the inner and outer layers overlap with each other and the catheter tube stiffens to achieve a more rigid state.

In the preferred embodiment, the tube is a diagnostic microcatheter with walls strong enough to handle high pressure injections of intravascular radio-opaque contrast. The lengths x and y are 1-5 mm, with y>x. The microcatheter is used to navigate second and third order vessels within patients during interventional radiological, cardiac, or surgical procedures. FIGS. 4A-4I show different embodiments in which different segments of the two layers comprise different materials, have different lengths, or register in differing combinations to achieve different bending characteristics. As shown in FIGS. 4J-4K, the proximal end 100 of the catheter can comprise a handle in which a proximal stop 110 can be used with a thumb knob 104 and one or more spring elements 102 to actuate relative movement between the two layers 20, 22. This can be used with a guidewire positioned within central lumen 120 to manipulate the distal end of the catheter through a sequence of turns in which a physician can navigate through interconnected lumens within the body.

Figure 5:
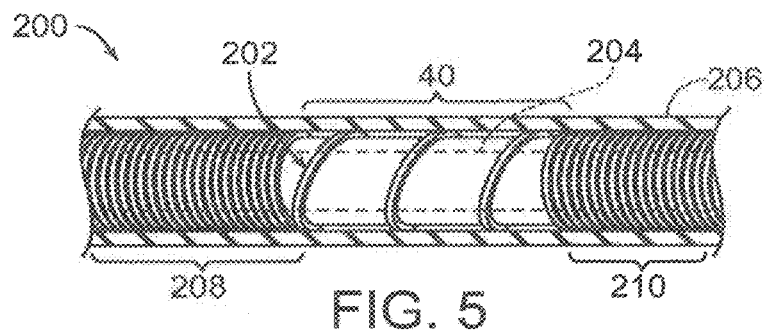
FIGS. 5-9 illustrate sectional views of methods of forming catheters in accordance with preferred embodiments of the invention.

In another preferred embodiment, a catheter layer 200, shown in FIG. 5, can comprise a variable pitch coil 202 mounted on an inner tube or liner 204 and covered with an outer polymer 206 to provide a flexible region 40, surrounded by stiffer regions 208, 210. Thus, the layer 200 can include a plurality of alternating segments of higher and lower stiffness. A second layer having an identical structure, except with a larger diameter, can be paired with layer 200 which is inserted within the second layer as described herein to form a flexible catheter that can be adjusted so that the alternating flexible and stiff regions can either be aligned with each other, or moved out of alignment, to provide a flexible or more rigid structure, respectively. Note that the stiffness of each segment can be selected by adjusting the pitch, or number of windings, within a given segment. Thus, stiff regions have a greater pitch and flexible regions have a smaller pitch.

Figure 6:
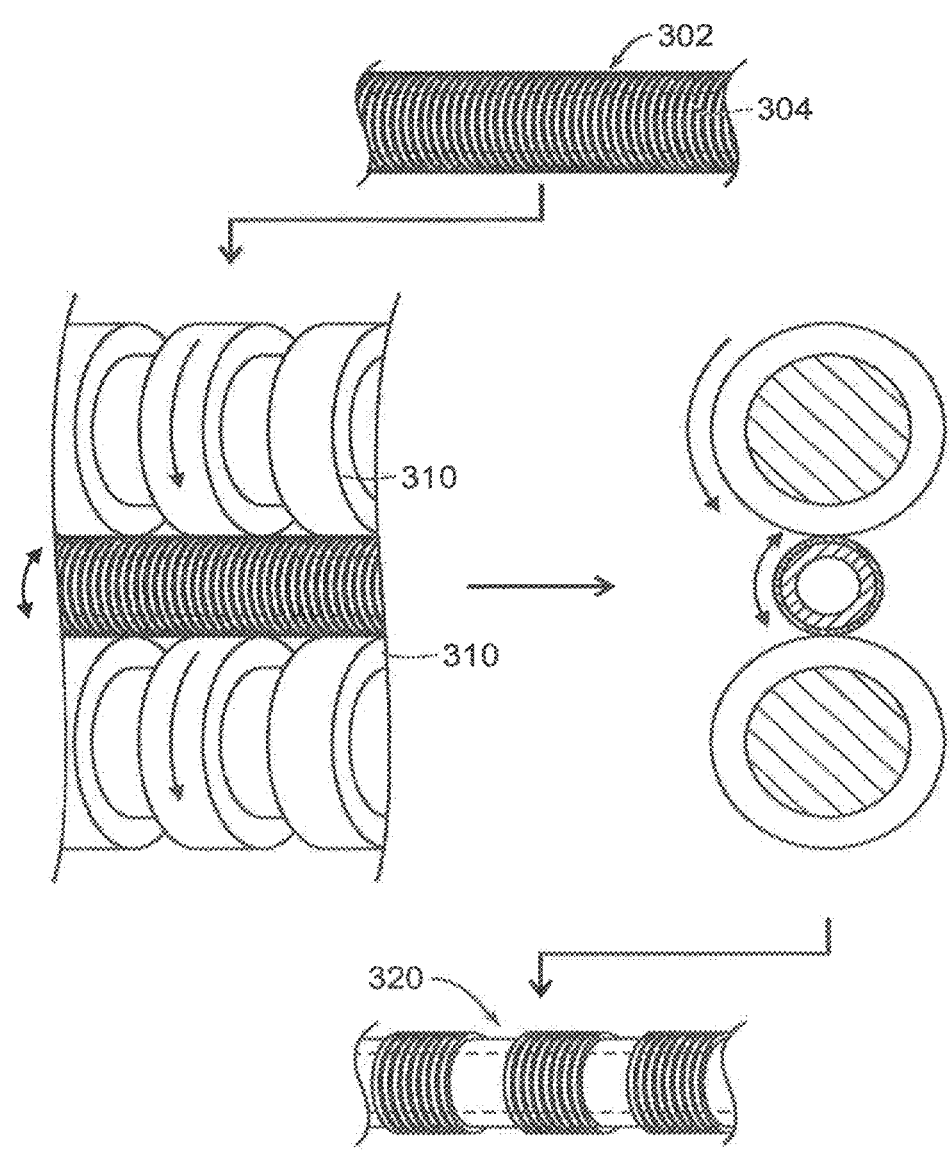
Figure 7:
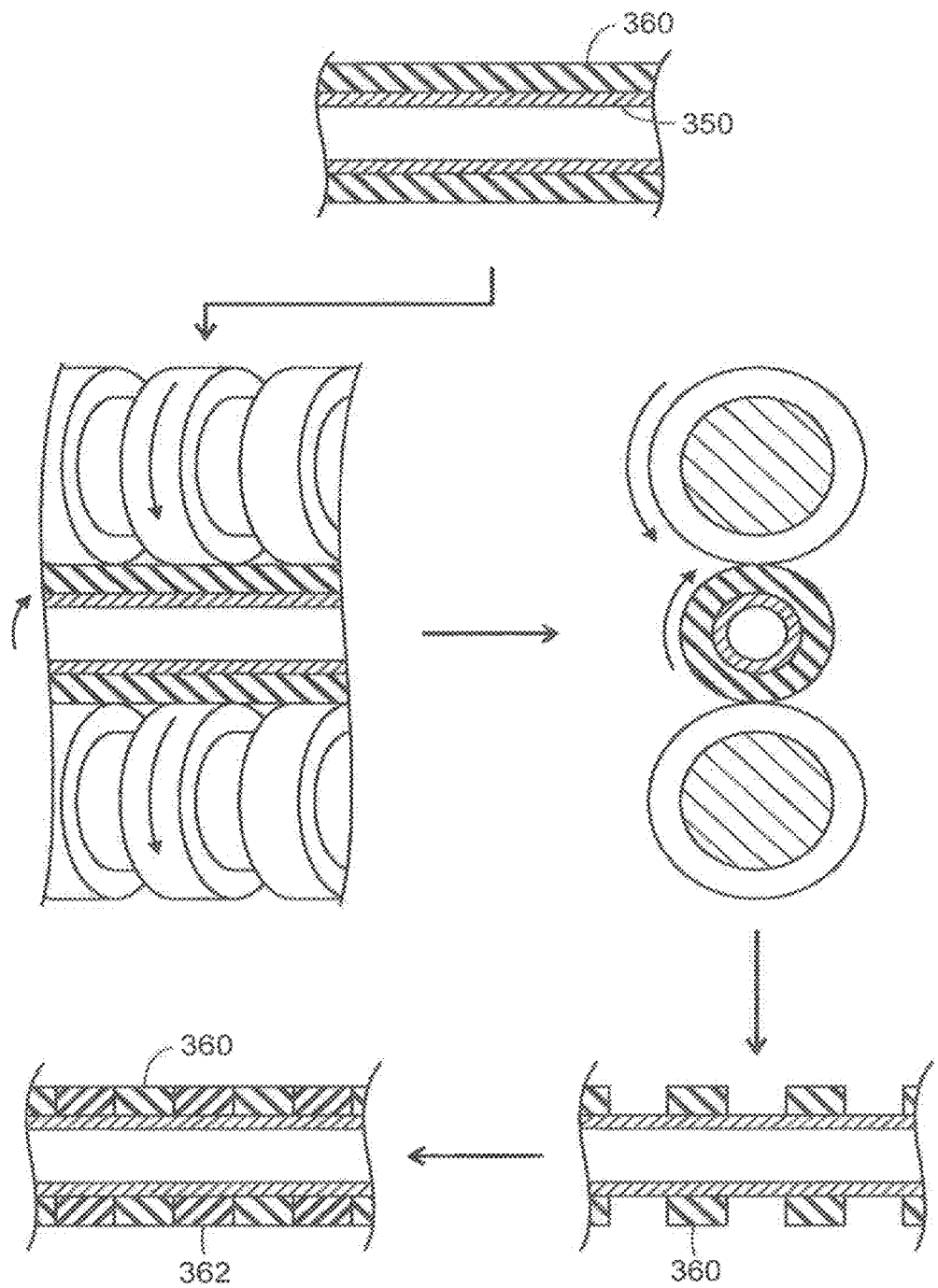

In a preferred method of making a catheter having adjustable stiffness as shown in FIG. 6, an inner liner 304 can be mounted with a coil braid 302. Grinding wheels 310 can form intervals to form alternating stiff and flexible regions. Another preferred method shown in FIG. 7 first forms a polymer layer 360 around an inner liner 350. Grinding wheels can form spaces and a second polymer layer 362 can be deposited in the spaces to form a composite structure of alternating segments.

Figure 8:
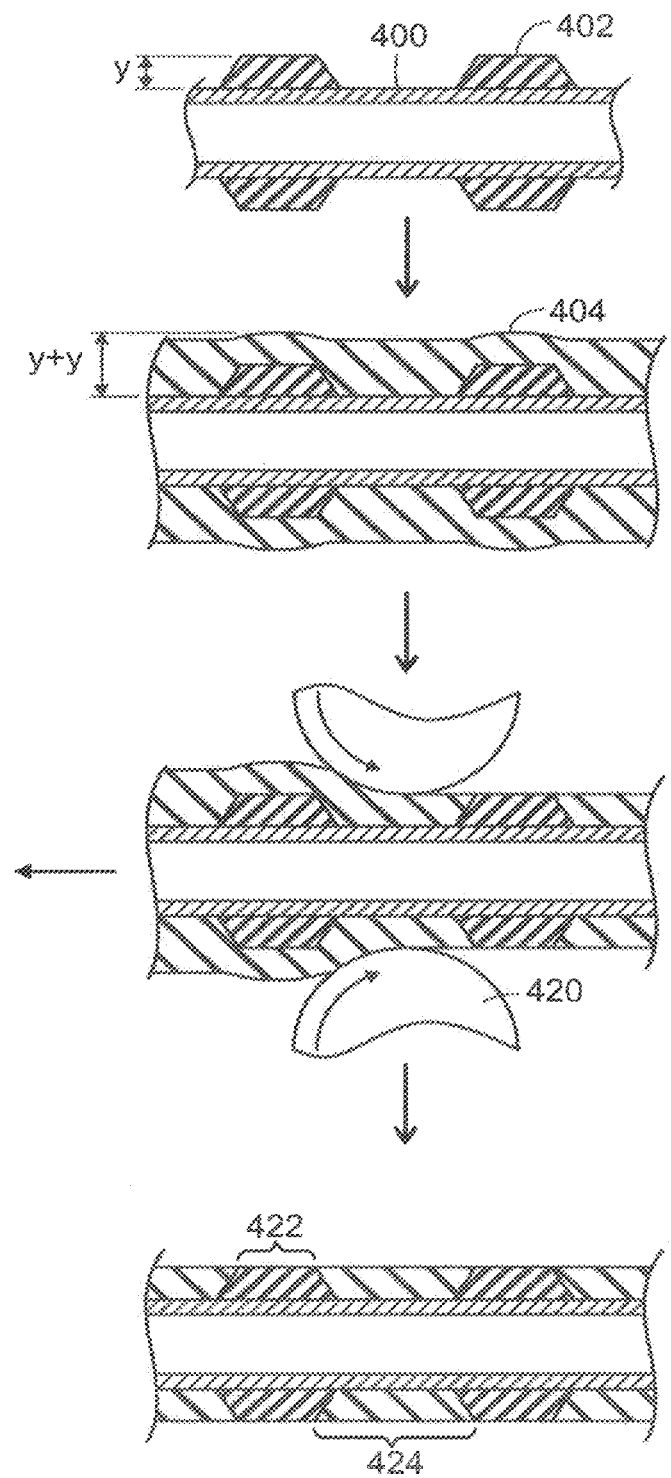
Figure 9:
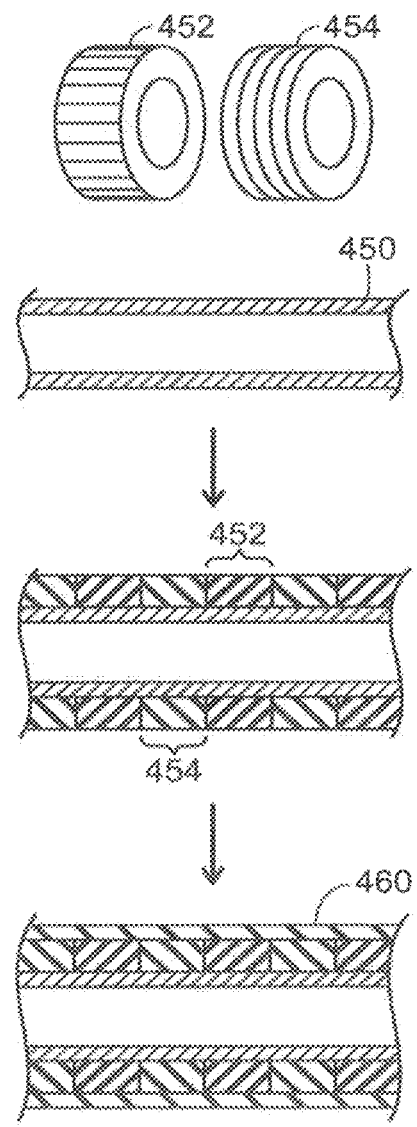

In FIG. 8, another preferred method of fabrication selectively deposits a polymer 402 to form segments on liner 400. A third polymer layer 404 can be formed and ground with grinding element 420 to form alternating stiff 422 and flexible 424 regions. In FIG. 9, stiff 452 and flexible tubes 454 can be positioned along a liner 450 which are then coated with an outer polymer 460 to secure the segments in place.

Figure 10:
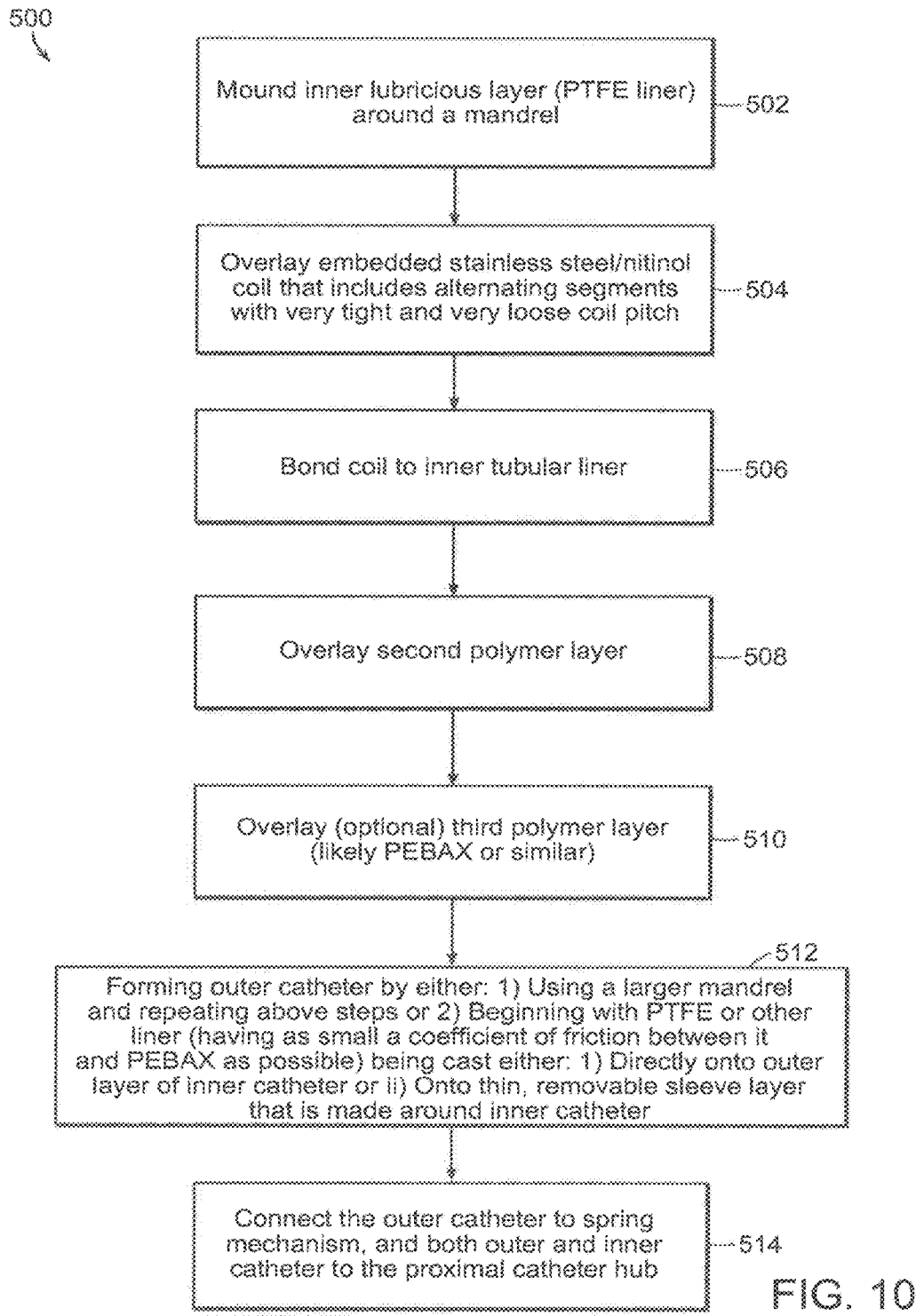
FIGS. 10-14 are process sequence diagrams of methods for fabricating adjustable stiffness catheters in accordance with preferred embodiments of the invention.

Shown in FIGS. 10-14 are process sequences illustrating steps for fabricating catheters in connection with preferred embodiments of the invention. In FIG. 10, the process 500 includes mounting a liner on a mandrel 502, mounting coil elements with different pitches 504, bonding these the liner 506, overlaying additional polymer layers 508, 510, assembling the different layers 512, and connecting the 514 actuator.

Figure 11:
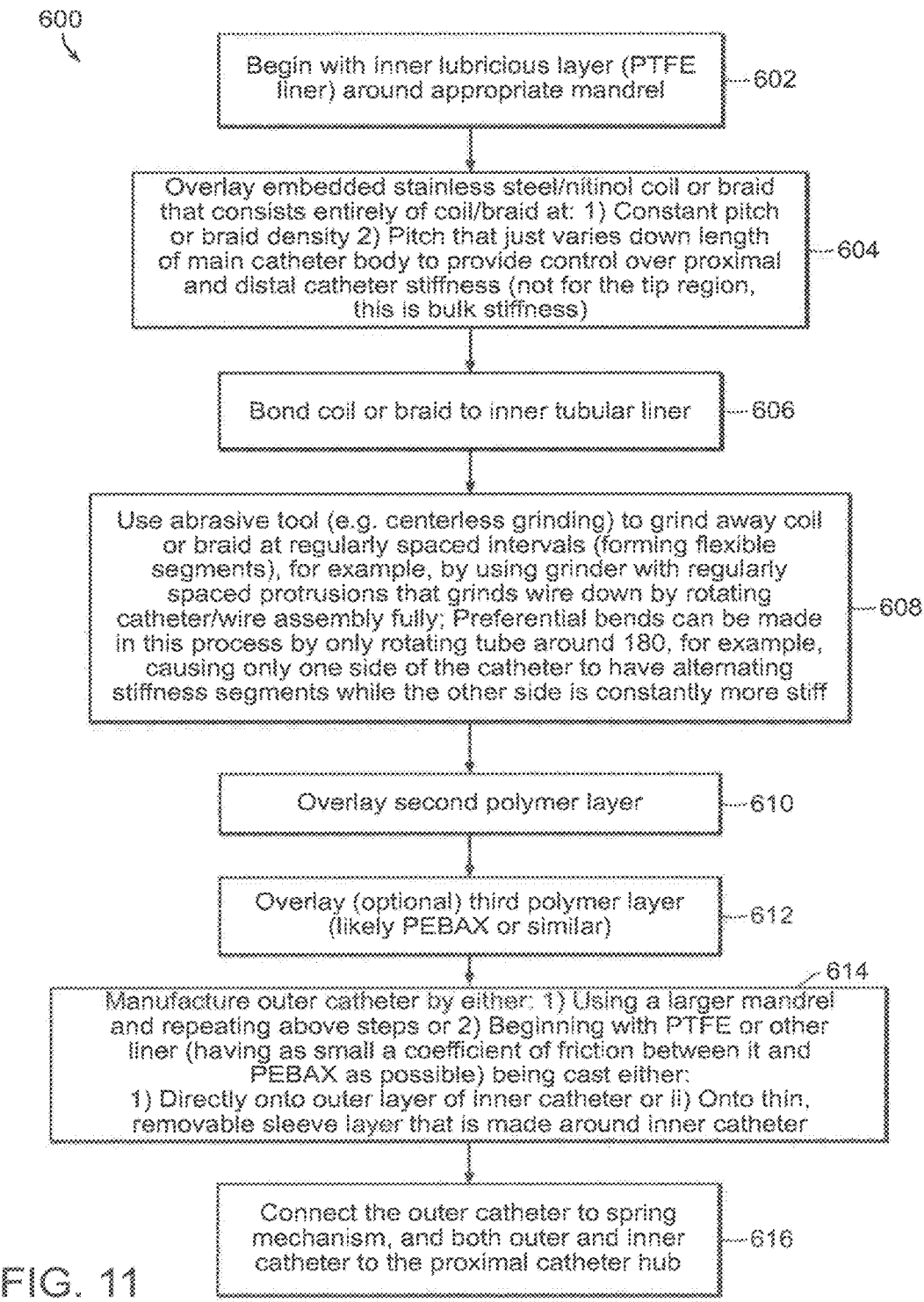
Figure 12:
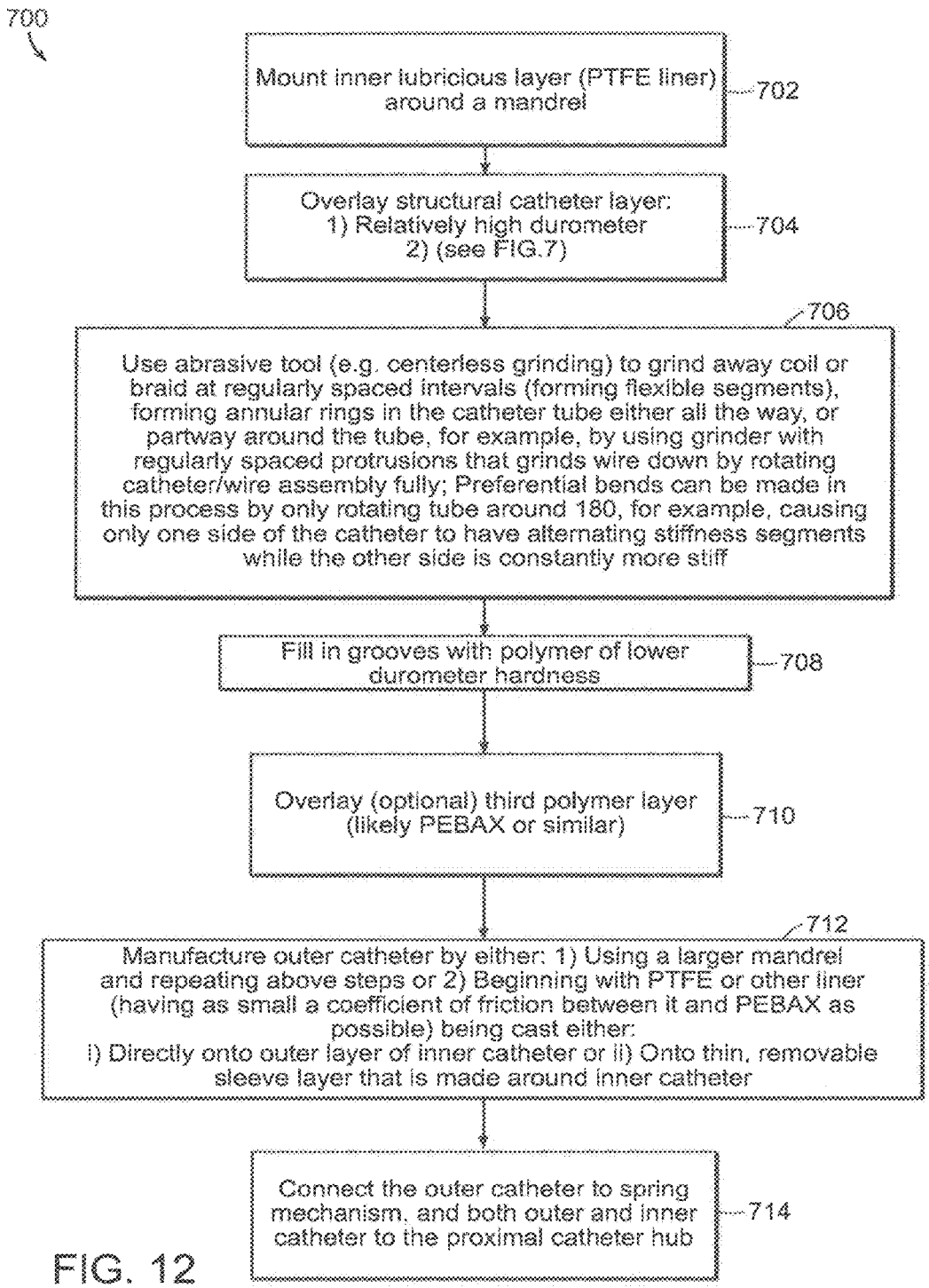
Figure 13:
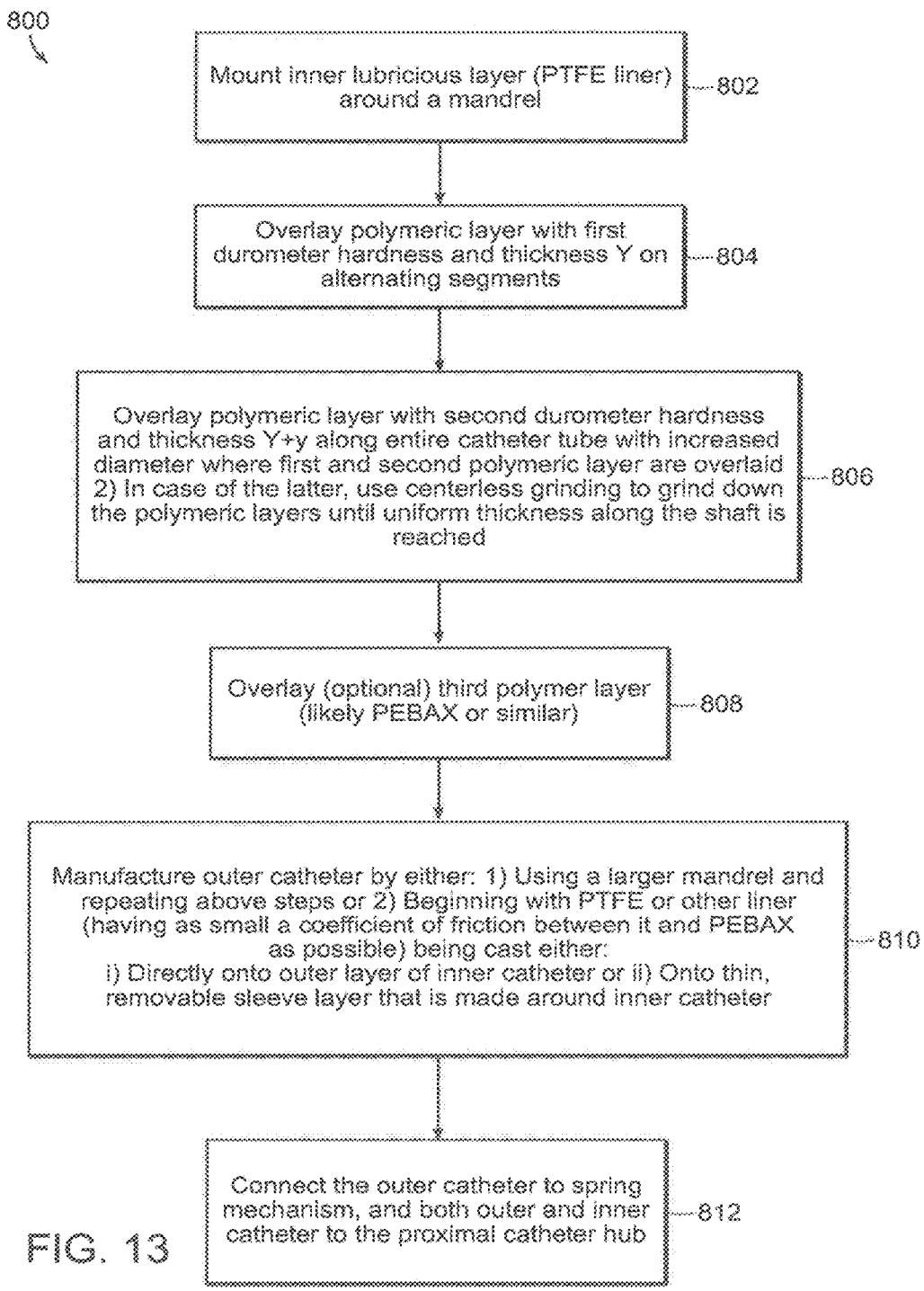
Figure 14:
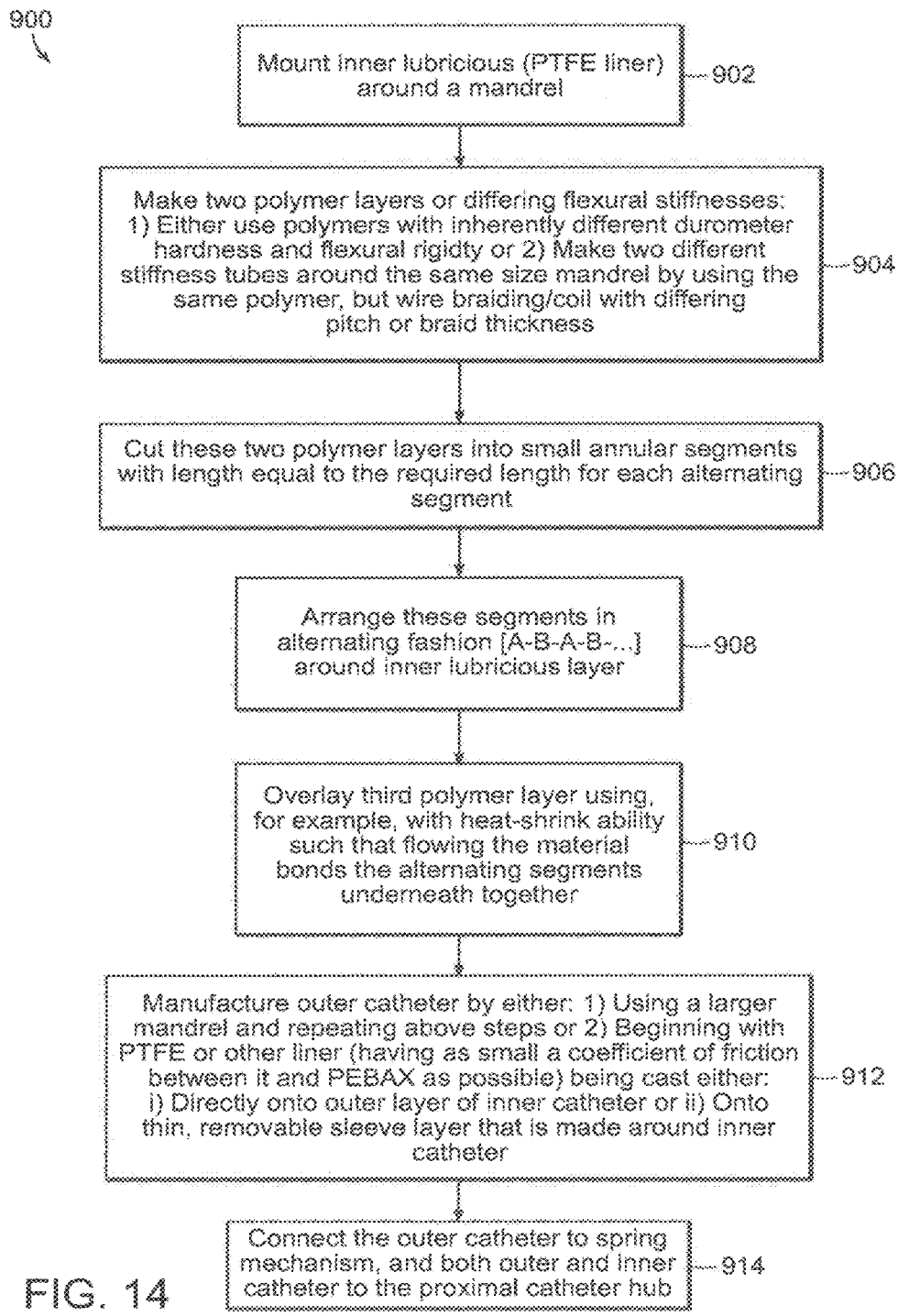

In the method 600 of FIG. 11, a layer is formed on a mandrel 602, form a braid or coil 604 and bonding thereof to a liner 606. A second polymer is overlayed 610, followed by an optional third layer 612. An outer tube is formed 614 and connected to a handle 616. A centerless grinding tool can be used to remove portions 608 of material to form segments. In the method 700 of FIG. 12, grooves formed by centerless grinding 706, for example, can be filled with a polymer of lower durometer 708 to form alternating segments of different durometers in a given layer. This is followed by outer catheter fabrication 712 and connection to a catheter hub or handle 714. In the method 800 of FIG. 13, with steps 802 and 804 followed by an overlying layer formed 806 with a third polymer can be formed over adjacent segments of different durometers along with steps 808, 810 and 812. In the method 900 of FIG. 14, two polymer layers can be formed 902, 904 on the same mandrel and then cut to selected lengths 906 for mounting on a selected liner in alternating fashion 908. These segments can then be secured in place with a third polymer layer or adhesive or a heat shrink material to secure the segments in place 910, 912 and 914.

Current vascular catheters and wires generally employ a different technique to engage second- or third-order vessels. A common problem occurs when small tortuous vessels prevent a catheter from being advanced because of sharp turns. This step is often the most time-intensive and unpredictable component of a procedure. Failure to advance is often due to the catheter being too soft and unable to traverse a sharp bend over a wire, or too stiff, causing the catheter and wire to disengage from the target vessel altogether. Ideally, an advancing catheter needs to be flexible when making initial sharp turns, but stiff enough to allow effective advancement into the vessel to obtain enough purchase for either further advancement or deployment of contrast materials, medication, or therapeutic devices.

The present invention is useful for any application that requires the operator to navigate a tube through a torturous tubular structure in the body. Preferred embodiments comprise vascular microcatheters, which can be used for procedures ranging from thrombolysis of cerebral artery occlusions to the coiling of bleeding mesenteric arteries. However, the invention provides a suitable solution to similar problems found in endoscopic procedures involving the GI and GU tracts as well as solving problems that frequently occur in cardiac procedures involving intravascular ultrasound catheters. Finally, simple and robust variable-stiffness catheters may also be in industrial applications involving drilling and exploration.

The catheters of the present disclosure can be used in a variety of different diagnostic and therapeutic procedures. For example, in certain embodiments, the catheters of the present disclosure can be used to sample or delivery fluids to selected anatomic sites. Examples of various diagnostic and therapeutic procedures that may be performed using fluids delivered or obtained through the catheters can include adrenal vein sampling: (e.g., sampling blood from several veins surrounding the adrenal glands in order to determine levels of aldosterone; neurovascular (including carotid, cerebral, and spinal vessels) diagnostic or therapeutic procedures; injection of thrombolytics to break up clots for ischemia treatment; contrast or MR angiography used to identify peripheral vascular disease and plan for future surgical intervention; catheter-based imaging of mesenteric artery to detect or rule out aneurysm, thrombosis, ischemia, or to locate the source of gastrointestinal bleeding; detection of portal hypertension and cirrhosis; imaging of the celiac artery to detect or rule out aneurysm, thrombosis, ischemia, or to locate the source of gastrointestinal bleeding; confirmation or detection of vascular anatomy and patency of hepatic vasculature prior to surgical intervention, for example for liver transplant; catheter-based delivery of contrast for gastric, pancreaticoduodenal, spenic, renal, thoracic, intercostal, coronary, or pulmonary angiography catheter-based delivery of contrast into biliary tree for imaging the biliary network; selective catheter angiogiography to identify anastomoses for percutaneous transluminal angioplasty (PTA) or surgical repair and/or selective catheter angiography to identify anastomoses for PTA or surgical repair; catheter-based injection of contrast agents for imaging lymph vessels to detect cancer metastasis; and/or injection of radiocontrast agents into the urinary tract for diagnostic imaging In other embodiments, solids can be delivered using the devices of the present disclosure. As discussed further below, smaller solid agents can be delivered directly by removing the guidewire and then introducing the agents through the microcatheter. For larger agents, however, the inner layer 20 may be removed to increase the inner diameter of the system. The devices of the present disclosure can be used to deliver embospheres (20 µm to 2000 µm, or 0.0008" to 0.008"), coils (0.01" to 0.4"), gelfoam (variable, typically ~0.25"), or mechanical thrombectomy devices (stentrievesr). At the 3 French OD scale, agents up to 0.018" can be delivered without removing the inner catheter, and for larger agents the inner layer may be removed. As examples, the devices of the present disclosure can be used for neurovascular aneurysm coiling, including aneurysms within the circle of Willis, cerebral arteries (posterior, anterior, and middle, up to 2nd order branches), and spinal vessels (aneurysm sizes 2-20 mm); transhepatic arterial chemoembolization (same requirements as hepatic arteries) for tumors; coiling or embolization of hepatic arteries; embolization of gastric artery to prevent aneurysm rupture or to cut off blood supply to a portion of the stomach producing the hormone ghrelin, which can lead to decreased feeding and weight loss in obese individuals; splenic artery coiling/embolization for aneurysms or pseudoanuerysms (aneurysm sizes 5-20 mm); gastroduodenal arterial coiling (aneurysm sizes 3-15 mm) for pseudoaneuryms; superior mesenteric artery embolization/coiling for aneurysms/pseudoaneurysms; mesenteric artery branch embolization/coiling for small bowel bleeding; colonic (right, middle, left) artery branch embolization or coiling for GI bleeding; rectal artery branch embolization or coiling for bleeding; uterine artery branch embolization or coiling (for uterine fibroids, uterine bleeding); pulmonary arterial embolization for treatment of pulmonary arteriovenous malformations, aneurysm, or bleeds; and lymphatic or thoracic duct coiling to prevent leakage of lymphatic fluids into the thoracic duct by selectively blocking the leaking vessels.

The devices of the present disclosure can further be used to deliver various therapeutic agents or therapies. As examples, the devices can be used for venous sclerosing treatments to selectively deliver sclerosing agents or fiber optic lasers to specific varicose veins in order to target their dissolution. Furthermore, the devices can be used to retrieve objects within a body lumen, include stents, thrombotic filters, unwanted foreign bodies, or instruments accidentally dislodged during surgical or radiological procedures.

In addition, in certain embodiments, the devices of the present disclosure can be fitted with a camera to be placed into a vessel or other cavity in order to image the area in question. Since cameras must fit within the inner diameter of the assembly (or the inner diameter of the outer catheter), these procedures may require slightly larger catheter systems, perhaps up to 5 French. Visualization using optical cameras may be employed in GI/Biliary applications imaging of the esophagus, stomach, and proximal small bowel; colonoscopy; ERCP (endoscopic retrograde cholangiopancreatography); laparoscopic procedures; mediastinoscopy; rhinoscopy, otoscopy; laryngoscopy; bronchoscopy; neurosurgical scoping; urological procedures; cystoscopy; ureteroscopy; prostatectomies; colposcopy; hysteroscopy; falloposcopy; and arthroscopy or visualization of any joint or musculoskeletal structure. In addition, the devices of the present disclosure may be used to drain or place tubes in various anatomic sites including, urinary catheters; urethral or bladder catheters; percutaneous nephrostomy tubes; abdominal/pelvic cavity tubes; general drains for abscesses or fluid collections; chest tubes; thoracostomy tubes; devices for paracentesis or thoracentesis; neurological devices; and ventriculostomy devices.

The devices of the present disclosure can be used in a variety of angioplasty or stenting procedures, including, but not limited to carotid stenting or angioplasty; vertebral artery stenting or angioplasty; spinal artery angioplasty; peripheral vascular stenting or angioplasty (lower or upper extremity); superior mesenteric artery stenting or angioplasty; celiac stenting or angioplasty; hepatic artery stenting or angioplasty; arteriovenous graft angioplasty; vascular anastomoses stenting or angioplasty (hepatic artery, vein, portal vein, renal artery, mesenteric artery anastomoses for transplants); biliary ballooning or stenting; pancreatic duct ballooning or stenting; esophageal ballooning or stenting; duodenal ballooning or stenting; colonic ballooning or stenting; and urinary tract stenting or ballooning A variety of different sizes and configurations of devices can be selected depending on the specific clinical application. It should be appreciated that the specific size and configuration may vary based on patient-specific factors, clinical situations, and/or clinician preference. Table 1, however, provides typical specifications for various applications, including an expected radius of curvature that the device should obtain for effective use. The presently disclosed devices provide advantages in that they can be produced with a range of sizes and shapes to provide systems for treatment of many different anatomic sites and conditions, and can be scaled to allow for a desired radius of curvature, which may be a critical factor in determining whether or not the device can reach a target site.

TABLE 1

Typical device specifications.

| Type of vessel/ technique | Req. catheter size | Req. tip length | Min. radius of curvature | Vessel diameter |
|---|---|---|---|---|
| Adrenal vein sampling | 2-4 Fr | 3-5 cm | 3 mm | 2-7 mm |
| Neurovascular | 1.5-4 Fr | 1-10 cm | 5 mm | |
| Upper and lower extremity | 1.5-6 Fr | 1-10 cm | 5 mm | |
| Mesenteric artery | 2-4 Fr | 1-10 cm | 5 mm | |
| Celiac trunk | 3-5 Fr | 1-10 cm | 5 mm | |
| Hepatic arteries/veins | 2-4 Fr | 1-10 cm | 5 mm | |
| Gastric arteries | 2-4 Fr | 1-10 cm | 5 mm | |
| Pancreaticoduodenal arteries | 2-4 Fr | 1-10 cm | 5 mm | |
| Splenic arteries | 2-4 Fr | 1-10 cm | 5 mm | |
| Renal arteries or veins | 2-4 Fr | 1-10 cm | 5 mm | |
| Thoracic or intercostal arteries | 2-4 Fr | 1-10 cm | 5 mm | |
| Pulmonary arteries and veins | 2-6 Fr | 1-5 cm | 5 mm | |
| Coronary arteries | 1.5-3 Fr | 0.5-5 cm | 3 mm | |

TABLE 1-continued

Typical device specifications.

| Type of vessel/ technique | Req. catheter size | Req. tip length | Min. radius of curvature | Vessel diameter |
|---|---|---|---|---|
| Arterial anastomoses | 2-4 Fr | 1-10 cm | 3 mm | |
| Bile duct anastomoses | 2-10 Fr | 1-15 cm | 5 mm | |
| Bile duct cholangiogram | 2-8 Fr | 1-10 cm | 3 mm | |
| Bowel anastomoses | 4-16 Fr | 5-20 cm | 10 mm | |
| Lymphangiography | 1.8-4 Fr | 1-10 cm | 5 mm | |
| Urinary tract imaging | 2-10 Fr | 1-10 cm | 5 mm | |
| AV graft angioplasty | 2-5 Fr | 1-10 cm | 5 mm | |
| EGD | 4-20 Fr | 5-20 cm | 5 mm | |
| Colonoscopy | 4-25 Fr | 5-20 cm | 5 mm | |
| Bronchoscopy | 2-4 Fr | | | |
| Cytoscopy/ ureteroscopy | 4-12 Fr | | | |
| Hysteroscopy | 2-5 Fr | | | |
| Falloposcopy | 1.5-4 Fr | | | |
| Urethral catheter | 8-20 Fr | | | |
| Percutaneous nephrostomy | 4-15 Fr | | | |
| General drains | 4-40 Fr | 1-10 cm | | |
| Paracentesis | 4-8 Fr | | | |

Figure 15:
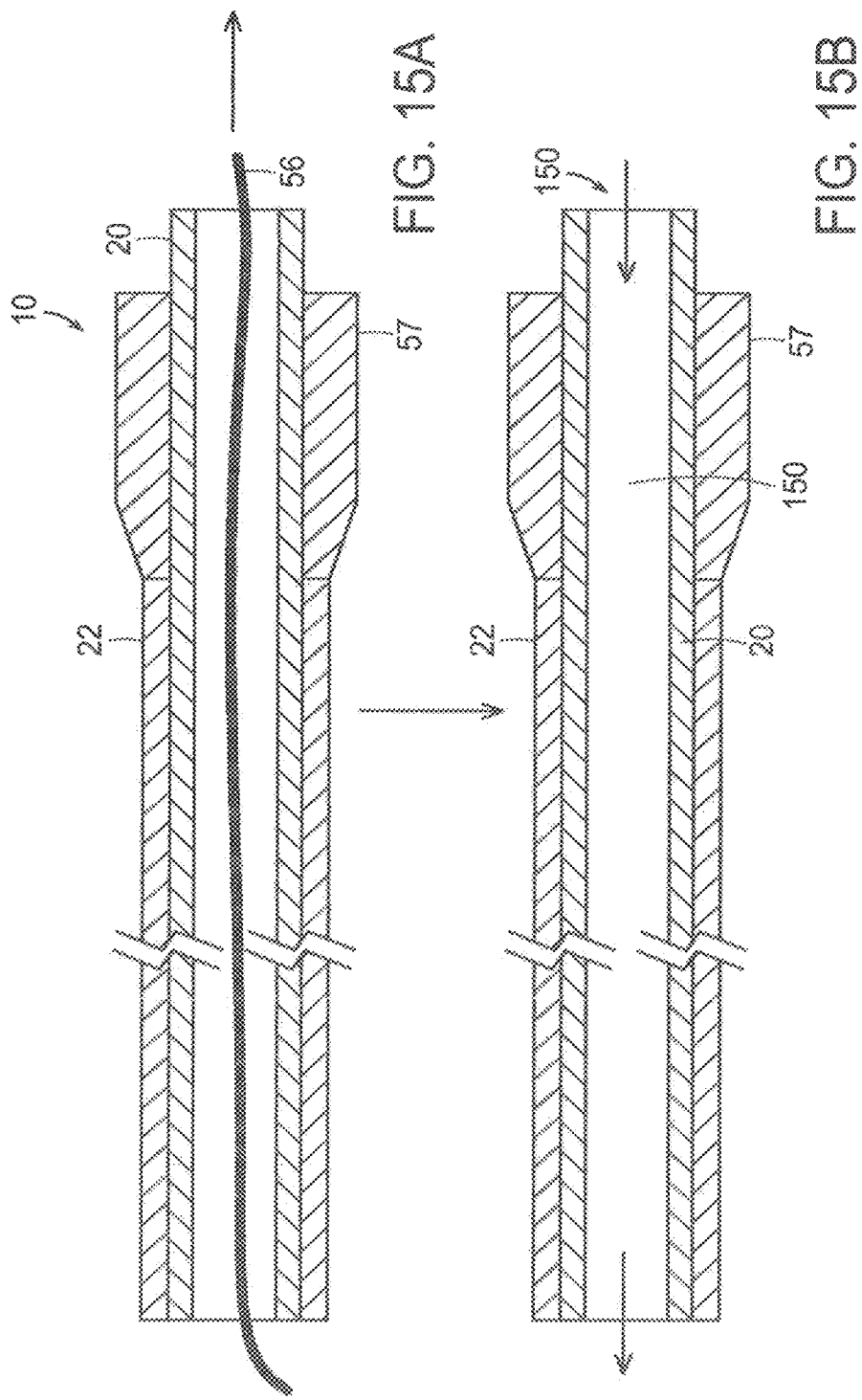
FIGS. 15A-15B illustrate side cutaway views of a catheter according to certain embodiments of the present disclosure.
Figure 16:
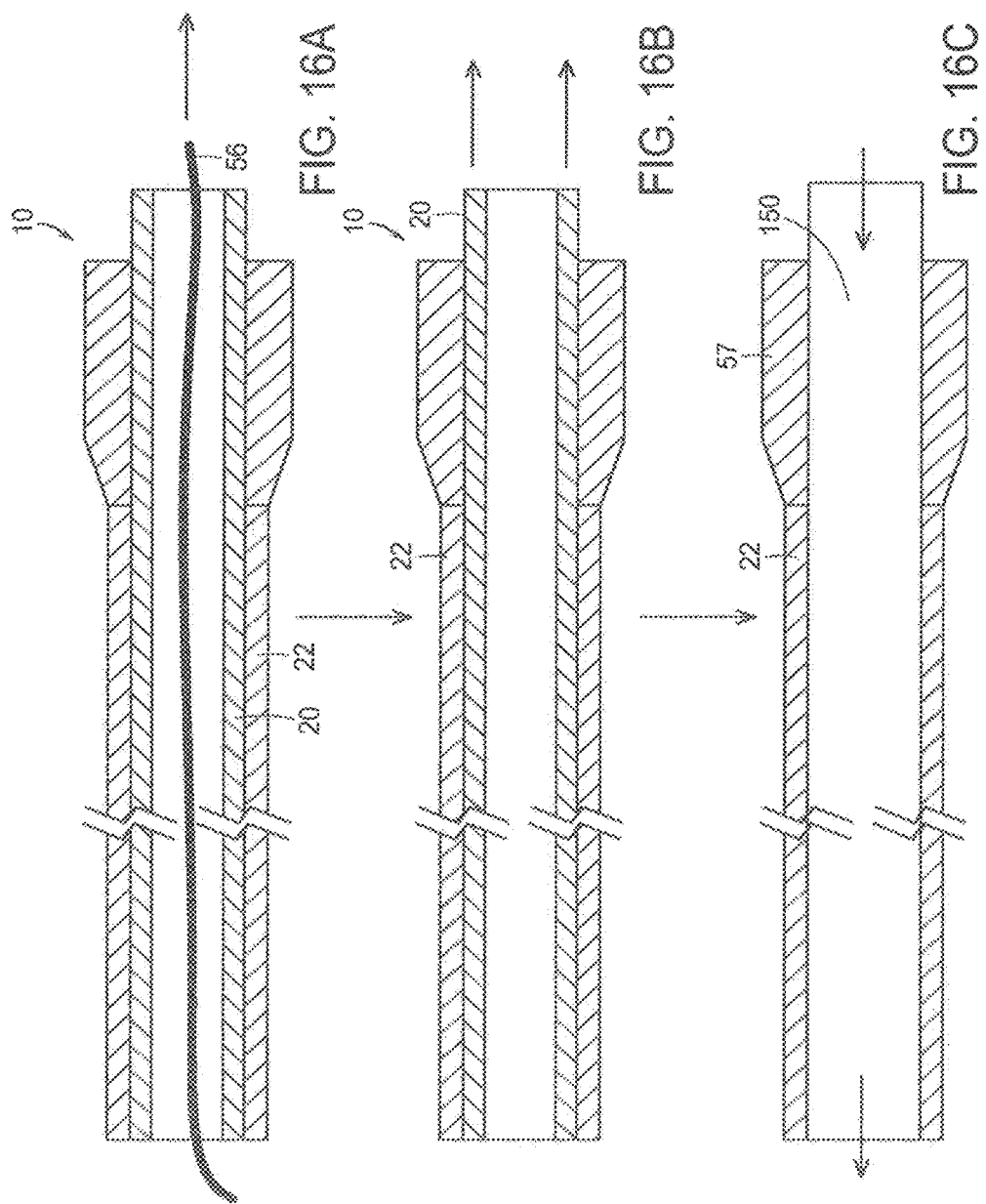
FIGS. 16A-16C illustrate side cutaway views of a catheter according to certain embodiments of the present disclosure.

FIGS. 15A-22B provide additional details illustrating how the devices of the present disclosure may be used in various clinical situations. FIGS. 15A-15B illustrate side cutaway views of a catheter 10 according to certain embodiments of the present disclosure. As shown, the catheter 10, comprises inner layer 20 and outer layer 22. In addition, the catheter 10 can comprise a guidewire 56 disposed within a lumen of inner layer 20. In certain embodiments, to deliver therapeutic or diagnostic agents, the guidewire 56 may be removed, thereby providing sufficient surface area within the catheter for effective flow of the agents. Alternatively, as discussed above, the inner layer 20, may be removed, as illustrated in FIGS. 16A-16C. As such, the lumen 150 will have an even greater cross-sectional area, which may be desirable for delivery of solid materials or for insertion of devices such as balloons or stents.

Figure 17:
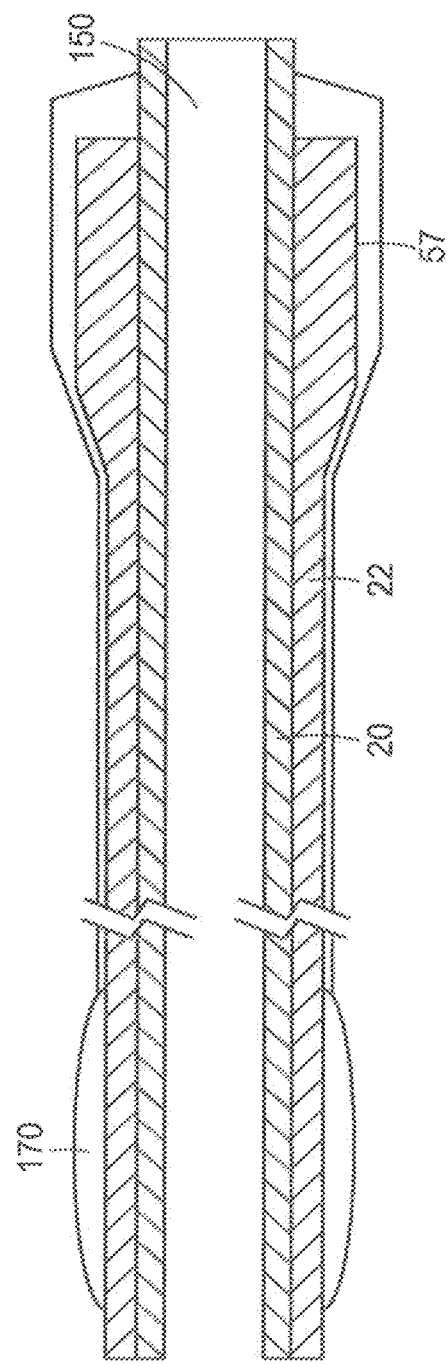
FIG. 17 illustrate a side view of a catheter including a balloon treatment device according to certain embodiments.

As discussed previously, the devices of the present disclosure can be used for therapeutic interventions, including balloon dilation and/or stenting. FIG. 17 illustrates a side view of a catheter including a balloon treatment device according to certain embodiments; and FIGS. 18A-18C illustrate side cutaway views of a catheter used to deliver a stent to a treatment site according to certain embodiments of the present disclosure. As shown, the devices 10 (FIG. 17) can include a balloon dilation device 170 positioned on a portion thereof, or alternatively, a separate balloon catheter may be advanced over a guidewire positioned using the catheters described herein, or may be passed through a lumen of the catheters described herein. Furthermore, a stent or other therapeutic device can be passed through a lumen of the disclosed catheters after optionally removing the inner layer and/or guidewire and inserting a secondary catheter 184 carrying a stent 180 and deployment device 182, as shown in FIGS. 18A-18C.

In some embodiments, the devices of the present disclosure can be used to access a desired anatomic site, and then to place a secondary catheter or treatment device. For example, FIGS. 19A-19C illustrate a method of positioning a secondary catheter or treatment device using various embodiments of the present invention. As shown in FIG. 19A, a device 10 can be deployed to a desired anatomic site, and may include a guidewire 56. After positioning the device 10 at the desired site, the catheter 10 may be removed, leaving only the guidewire 56 in place. Subsequently, a secondary device configured for a particular therapeutic or diagnostic application, but perhaps unable to be navigated to the desire site on its own, will be passed over the positioned guidewire 56, thereby allowing positioning of the secondary catheter 11 or treatment device.

Figure 20:
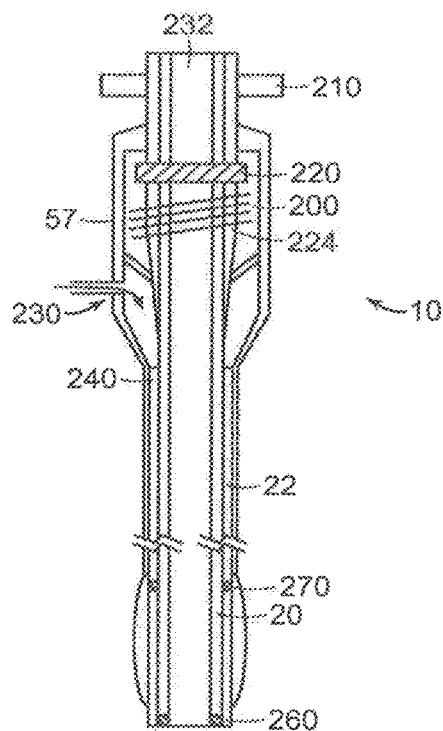
FIG. 20 illustrates a side cutaway view of a catheter with a handle region according to certain.
Figure 21A:
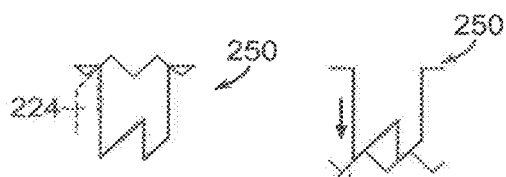
FIGS. 21A-21D illustrate components of an actuator in a handle region of a catheter according to certain embodiments.
Figure 21B:
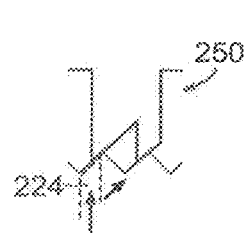
Figure 21C:
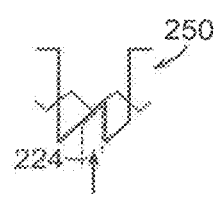
Figure 21D:
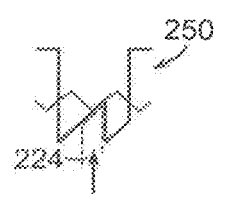

As noted above, the devices of the present disclosure can include a handle region 57, which can provide a variety of different structures and functional control for a clinician. FIG. 20 illustrates a side cutaway view of a catheter with a handle region 57 according to certain. And FIGS. 21A-21D illustrate components of an actuator in a handle region 57 of a catheter according to certain embodiments. As shown, the handle 57 can include a button 210, which can be attached to a cam 220, and cam follower 224. Further, as illustrated in FIGS. 21A-21D, the cam follower 224 can move along a path from an extended position FIG. 21B-21D, to a retracted position (FIG. 21A). As such, the cam follower 224, which is operably attached to at least one of the inner and outer layers 20,22 provides longitudinal movement of the layers 20,22 relative to one another. Furthermore, the inner and out layers are held in either an in register or out of register position relative to one another, similar to the mechanism used to hold a "click pen" in an extended or retracted position.

In addition, FIG. 20 illustrates various other components of the devices of the present disclosure. As noted above, the devices can be used to deliver fluid, e.g., for therapeutic or diagnostic applications, and the handle may include one or more fluid ports 230,232. In addition, the devices can include one or more radiopaque markers 260,270 on either or both of the inner or outer layers 20,22, thereby allowing visualization of the catheters during use, and assisting in determining if the catheter is in a stiffer or flexible state.

FIG. 20 further illustrates a space 240 between the inner and outer layers 20,22. The space 240 may vary based upon the particular clinical use and dimensions of the device. However, the space 240 should be sized to allow the devices to bend at a high radius of curvature without producing excessive frictional contact between the layers 20,22. In various embodiments, the space is 1-50 microns, or 30-70 microns, on all sides of the inner layer.

In various embodiments, in order to allow ease of movement through lumens, and in order to provide for movement of the inner and out layer 20,22 relative to one another, even during large bends, the surfaces of the layers may be treated to reduce the friction between various components. For example, FIGS. 22A-22B illustrate side cutaway views of catheters incorporating lubricious coatings 23, according to various embodiments. When rounding multiple tortuous bends with the catheter assembly, the increased area of direct contact between the two catheter layers 20,22 (due to pressing of the inner catheter against the one side of the outer catheter's inner surface) can generate friction that prevents shifting between the flexible and stiff states by restricting the movement of the inner catheter relative to the outer catheter. Accordingly, lubricioius coatings 23 may be used in order to reduce the coefficient of friction between the inner and outer catheter, and between the outer catheter and the anatomic sites such as blood vessel walls. The lubricating coatings 23 will be applied to the outer surface of the inner catheter, the outer surface of the outer catheter, and/or the inner surface of the outer catheter. Generally, the coatings 23 will be applied and cured prior to assembly of the inner catheter, outer catheter, and handle into a finished device.

In various exemplary embodiments, the coatings 23 may be made of the from a variety of materials include a PTFE liner added on top of a mandrel (to coat inner surface of catheter) or on top of the catheter while on a mandrel (to coat outer surface of catheter), a hydrophilic synthetic polymer network that is applied by dip or brush coating and cured to the catheter surface by heat treatment, a hydrophilic synthetic polymer network that is applied by dip or brush coating and cured to the catheter surface by UV treatment, a hydrophilic synthetic polymer network that is applied by gaseous activation of the catheter surface and subsequent grafting onto catheter surface by polymer from aqueous solution, and/or hydrophilic natural polymer network (such as those based on hyaluronic acid) that is bonded to a base coat layer attached to the catheter surface. Further, although the coatings 23 can have a variety of sizes and material properties, exemplary coatings may have a thickness between 1 and 10 micrometers and a coefficient of friction between 0.005 and 0.03, or a reduction of up to 90% compared to uncoated coefficients of friction. Compatible with pebax base materials, and with common methods of sterilization (EtO, gamma irradiation, etc.).

Figure 23A:
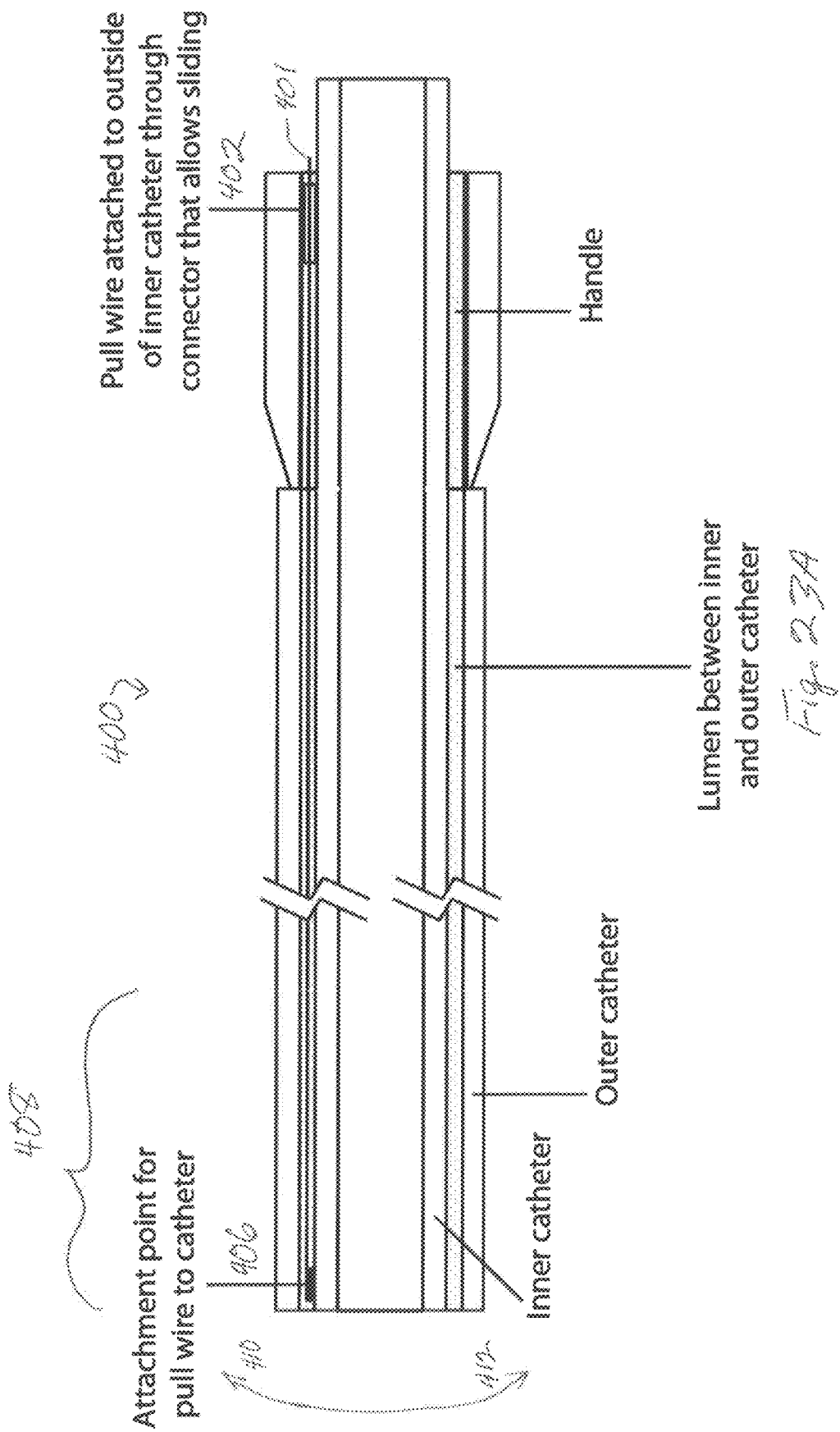
FIG. 23A illustrates a side cross-sectional view of a catheter pull wire according to preferred embodiments.

In preferred embodiments, it can be advantageous to provide further directional control of catheter delivery for the methods an devices described herein. Illustrated in FIG. 23A is a steerable coaxial catheter 400 formed by attaching a pull-wire 402 to an outside surface of an inner catheter, the pull-wire is connected at a fixed point 406 to the distal end 408 or tip of the inner catheter, and at the back end it is slide-able within a small range to bend the tip in two different directions 410, 412. Since the wire is internal to the outer catheter, it does not cause problems with abrasion of the vessel walls. This increases the difference between the inner diameter (ID) of the outer catheter and outer diameter (OD) of inner catheter depending on the thickness of the wire. A metal wire, such as stainless steel having a circular cross-section, a thickness in a range of 0.025-0.1 mm, and a column and tensile strength sufficient to avoid buckling or kinking is suitable for preferred embodiments. Alternatively, a channel formed in the outer surface of the inner catheter to receive the pull wire can also be used to reduce or eliminate a change in diameter.

Figure 23B:
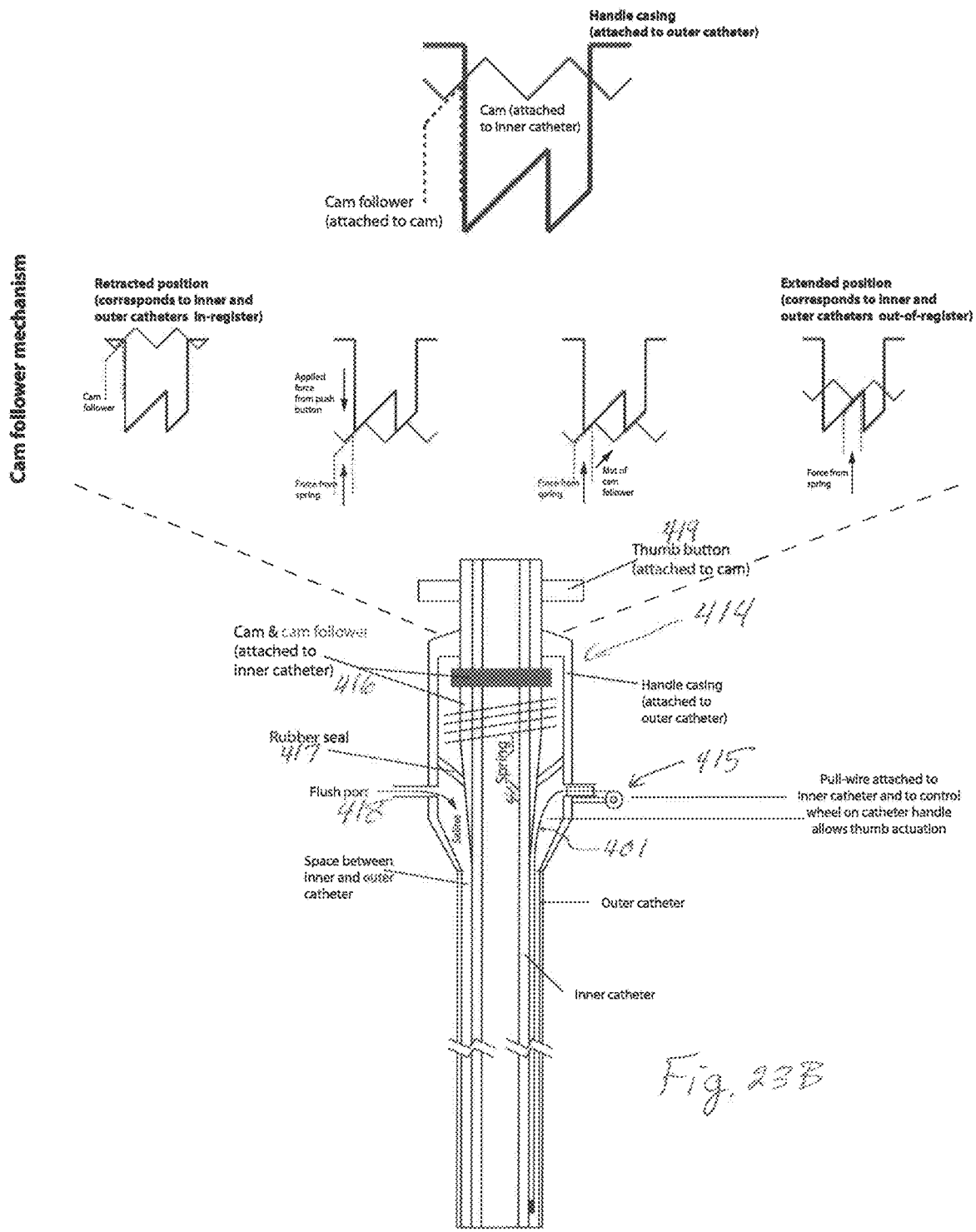
FIG. 23B illustrates a cross-sectional view of a catheter and handle in accordance with preferred embodiments.

Shown in FIG. 23B is a preferred embodiment in which a wire operative to bend or deflect the catheter to enable steering in a plurality of directions during delivery can be actuated by using a wire actuator 445 in the handle at the proximal end of the catheter. The actuator 415 can comprise a which rotated by a user's thumb to apply tension to the wire in both distal and proximal directions. Alternatively, a trigger operable by the user's forefinger can also be used to apply tension to the wire. A cam and cam follower mechanism 416 can be used with a spring 411 to control positioning of the inner and outer catheter elements. A flush port 418 can be used to delivery and remove fluid such as saline from the operative site.

Shown in FIG. 24 is a steerable coaxial catheter 420 created by attaching a pull-wire to an inside surface of the outer catheter. The pull-wire 422 is connected at a fixed point 424 to the interior of the distal end or tip of the outer catheter, and at the back end, it is slide-able within a small range to bend the tip in two different directions. Since the wire is internal to the outer catheter, it also does not cause problems with abrasion of the vessel walls. This can increase the difference between the ID of the outer catheter and OD of inner catheter. At the tip where the pull-wire is connected, the manufacturing is simplified by forming the fixed attachment point 426 for the pull-wire prior to assembling the flexible and stiff segments. The segments can be formed to preferably bend at one or more points at the distal end of the catheter or along the length of the insertion portion of the device.

Figure 25A:
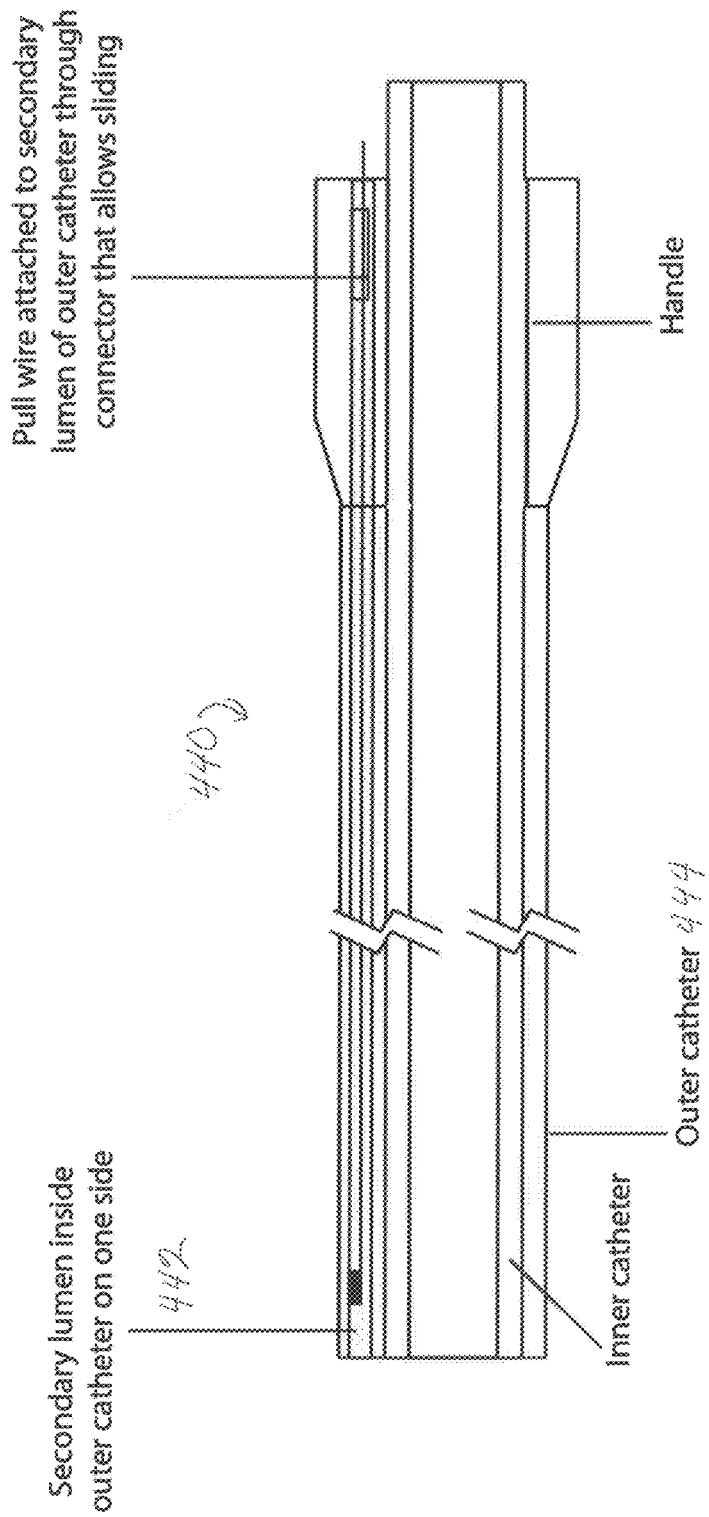
FIG. 25A illustrates a cross sectional view of a pull wire in a secondary lumen of an outer catheter in accordance with preferred embodiments.

FIG. 25A shows a steerable coaxial catheter 440 created by extending a pull-wire through a secondary lumen 442 of outer catheter 444. This does not require the difference between outer catheter ID and inner catheter OD to change, but can make the wall thickness of the outer catheter larger.

Figure 25B:
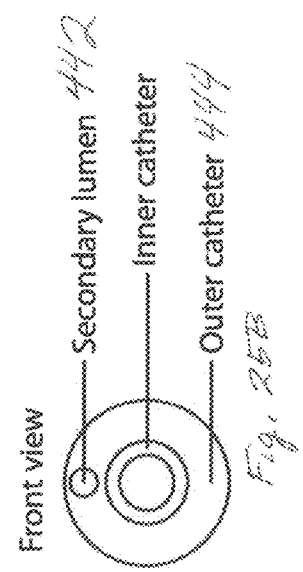
FIG. 25B illustrates a cross-sectional view illustrating a secondary lumen in the outer catheter body of a preferred embodiment.

FIG. 25B shows a cross-sectional front view illustrating a position of the lumen 442 relative to the inner catheter and outer catheter 444.

Figure 26A:
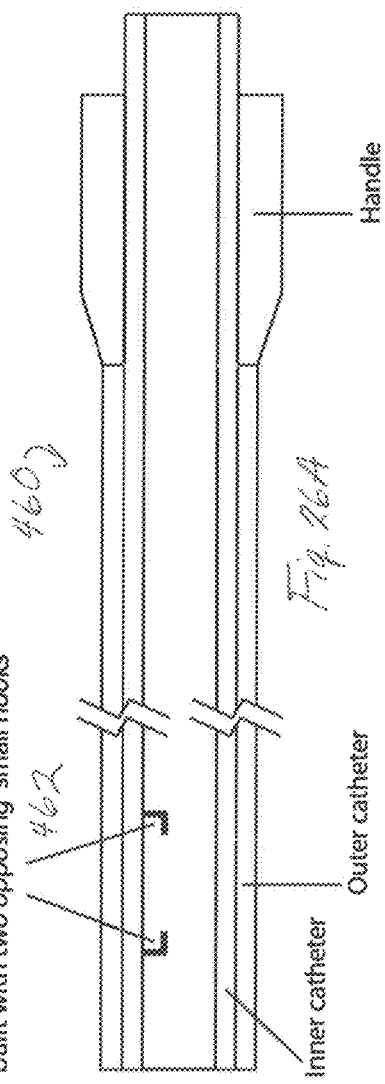
FIGS. 26A-26C illustrate a guidewire directional control embodiment in accordance with preferred embodiments.
Figure 26B:
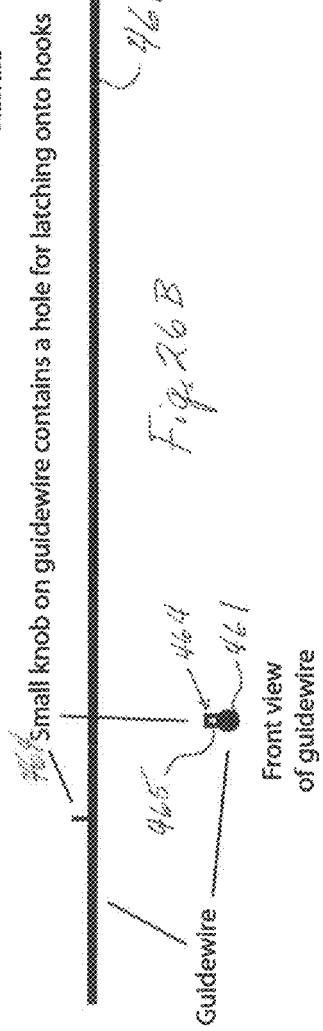
Figure 26C:
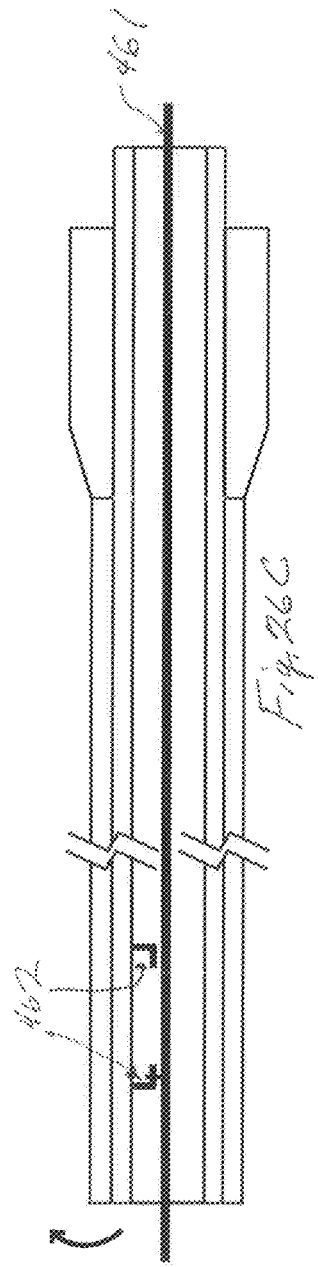

FIGS. 26A-26C show a steerable coaxial 460 catheter created by embedding a proximal and distal 'hook' or radial elements 462 near the tip inside the inner catheter, and combining with a guidewire 461 that can latch onto either hook to provide tension/compression for bending the tip. There are two opposing hooks 462 that can engage the inside of one of the segments of the inner catheter tip. The guidewire has a small addition, a protrusion 464 with a small hole 465 to fit over the hooks. When the guidewire engages the more distal hook (closer to the tip) and is pushed forward, it pushes in compression and bends the tip toward the side that the hooks are on. When the guidewire engages the proximal hook (further from the tip) and is pulled back, it pulls in tension and bends the tip away from the side that the hooks are located. The handle can include a tensioning mechanism that enables the user to push or pull the steering wire or cable to move the distal tip through a selected range of deflection angles. Preferred embodiments can utilize a plurality of pull wires to enable control in two or more directions. Fluorescence markers can be attached to the flexible portions of the catheter to enable visualization during delivery. The hooks 462 and guidewire element 464 can also comprise fluorescent markers to aid in visualization.

What has been described and illustrated herein is a preferred embodiment of the invention along with some of its variations. The terms, descriptions and figures used herein are set forth by way of illustration only and are not meant as limitations. Those skilled in the art will recognize that many variations are possible within the spirit and scope of the invention in which all terms are meant in their broadest, reasonable sense unless otherwise indicated. Any headings utilized within the description are for convenience only and have no legal or limiting effect.

The invention claimed is:

1. A method for guiding a catheter to a treatment site within a body comprising:
   inserting a tubular catheter into a neurovascular lumen within the body, the catheter having a flexible distal region including a first plurality of outer tubular segments comprising a first material, the outer tubular segments being spaced apart by regions comprising a different second material that have a different stiffness than the outer tubular segments;
   actuating relative longitudinal movement between the first plurality of outer tubular segments and a second plurality of inner spaced apart tubular segments to alter a bending stiffness of the flexible distal region; and
   advancing the catheter within the neurovascular lumen.

2. The method of claim 1, wherein the actuating step comprises sliding at least one layer within the catheter to alter the bending stiffness such that the distal region has a radius of curvature in a range of 2-6 mm.

3. The method of claim 1, further comprising advancing a guidewire through a central lumen of the catheter to select a lumen branch to advance the catheter to a treatment site.

4. The method of claim 1, wherein the actuating step comprises actuating relative movement of a first layer and a second layer, the first layer comprising alternating first regions of differing stiffnesses, and the second layer comprising alternating second regions of differing stiffnesses.

5. The method of claim 1, further comprising delivering a fluid to a site within the body.

6. The method of claim 1, further comprising delivering a treatment device to a site within the body.

7. The method of claim 6, wherein the step of delivering a treatment device comprises inserting at least one of a coil, a snare, a balloon, or a stent to a treatment site.

8. The method of claim 1, further comprising grasping a handle to move the catheter, the handle including an actuator to adjust a flexibility of the catheter.

9. The method of claim 1, further comprising percutaneously introducing the catheter into a neurovascular lumen, wherein the second inner spaced tubular segments comprises:
   an inner tube having a plurality of inner spaced regions having a first stiffness separated by a plurality of spaced inner segments having a greater stiffness than the plurality of inner spaced regions.

10. The method of claim 9, wherein the first plurality of outer tubular segments and regions comprises an outer tube.

11. The method of claim 10, further comprising actuating longitudinal translation wherein a layer is positioned between the inner tube and the outer tube.

12. The method of claim 11, wherein the layer comprises a flexible region of a polymer material.

13. The method of claim 8, further comprising inserting a fluid with the handle that comprises at least one fluid supply port.

14. The method of claim 1 wherein the inserting step comprises inserting the catheter having a size in a range of 1.5 to 4 French.

15. The method of claim 1 further comprising inserting a guidewire into the body to the treatment site and advancing the catheter into the neurovascular lumen along the guidewire to the treatment site.

* * * * *